(12) United States Patent
Harding et al.

(10) Patent No.: US 10,892,046 B1
(45) Date of Patent: Jan. 12, 2021

(54) SYSTEMS AND METHODS FOR DYNAMICALLY EXTRACTING ELECTRONIC HEALTH RECORDS

(71) Applicants: James A. Harding, Issaquah, WA (US); Mark W. Bowers, Langley, WA (US); Alejandro G. Carrillo, Seattle, WA (US)

(72) Inventors: James A. Harding, Issaquah, WA (US); Mark W. Bowers, Langley, WA (US); Alejandro G. Carrillo, Seattle, WA (US)

(73) Assignee: MultiScale Health Networks LLC, Seattle, WA (US)

(*) Notice: Subject to any disclaimer, the term of this patent is extended or adjusted under 35 U.S.C. 154(b) by 781 days.

(21) Appl. No.: 14/693,147

(22) Filed: Apr. 22, 2015

Related U.S. Application Data

(63) Continuation-in-part of application No. 14/463,542, filed on Aug. 19, 2014, now abandoned.

(60) Provisional application No. 62/039,059, filed on Aug. 19, 2014.

(51) Int. Cl.
*G16H 10/60* (2018.01)

(52) U.S. Cl.
CPC .................. *G16H 10/60* (2018.01)

(58) Field of Classification Search
CPC ........ G06Q 50/22; G06Q 50/24; G06F 17/30; G16H 40/20; G16H 10/60
USPC .......................................................... 705/3
See application file for complete search history.

(56) References Cited

U.S. PATENT DOCUMENTS

| | | | | |
|---|---|---|---|---|
| 6,374,262 B1* | 4/2002 | Kodama | ........... | G06F 17/30575 707/623 |
| 2002/0016718 A1* | 2/2002 | Rothschild | ............ | G06F 19/321 705/2 |
| 2005/0071194 A1* | 3/2005 | Bormann | ............... | G06Q 50/22 705/2 |
| 2005/0137910 A1* | 6/2005 | Rao | ........................ | G06Q 10/10 705/3 |
| 2005/0251540 A1* | 11/2005 | Sim-Tang | ........... | G06F 11/1471 |
| 2010/0198622 A1* | 8/2010 | Gajic | ..................... | G06Q 50/22 705/3 |
| 2011/0246876 A1* | 10/2011 | Chutani | ............... | A61B 8/4411 715/702 |
| 2012/0216179 A1* | 8/2012 | Sharma | ..................... | G06F 8/65 717/168 |

(Continued)

*Primary Examiner* — Hiep V Nguyen
(74) *Attorney, Agent, or Firm* — Benedict R. Dugan; Lowe Graham Jones PLLC

(57) ABSTRACT

Techniques for dynamically extracting electronic health records are described. Some embodiments provide an Operational Intelligence Platform ("OIP") that is configured to dynamically extract electronic health record data from a source customer database that represents health records in a hierarchical format, and store the extracted data in a clinical data engine that represents the health records in a manner that logically preserves the hierarchical format while providing a relational access model to the health records. The OIP may extract health-record data in substantially real-time by performing on-the-fly capture and processing of data updates to the source customer database. Such real-time extraction may be performed in cooperation with large scale, batch extraction of records from the source customer database.

19 Claims, 15 Drawing Sheets

(56) References Cited

U.S. PATENT DOCUMENTS

2013/0036090 A1* 2/2013 Akiyama .......... G06F 17/30578
707/624
2013/0054693 A1* 2/2013 Chennamadhavuni ......................
G06Q 30/0269
709/204

* cited by examiner

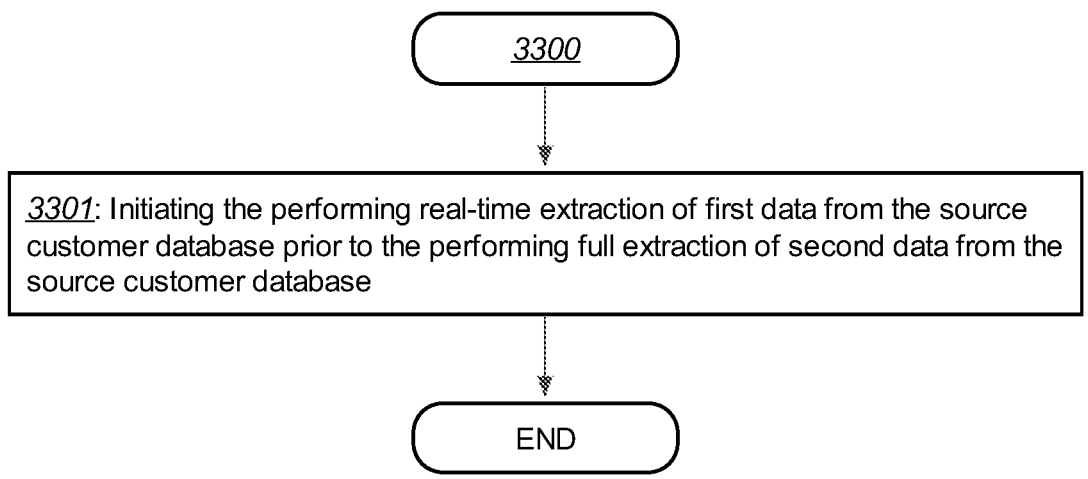

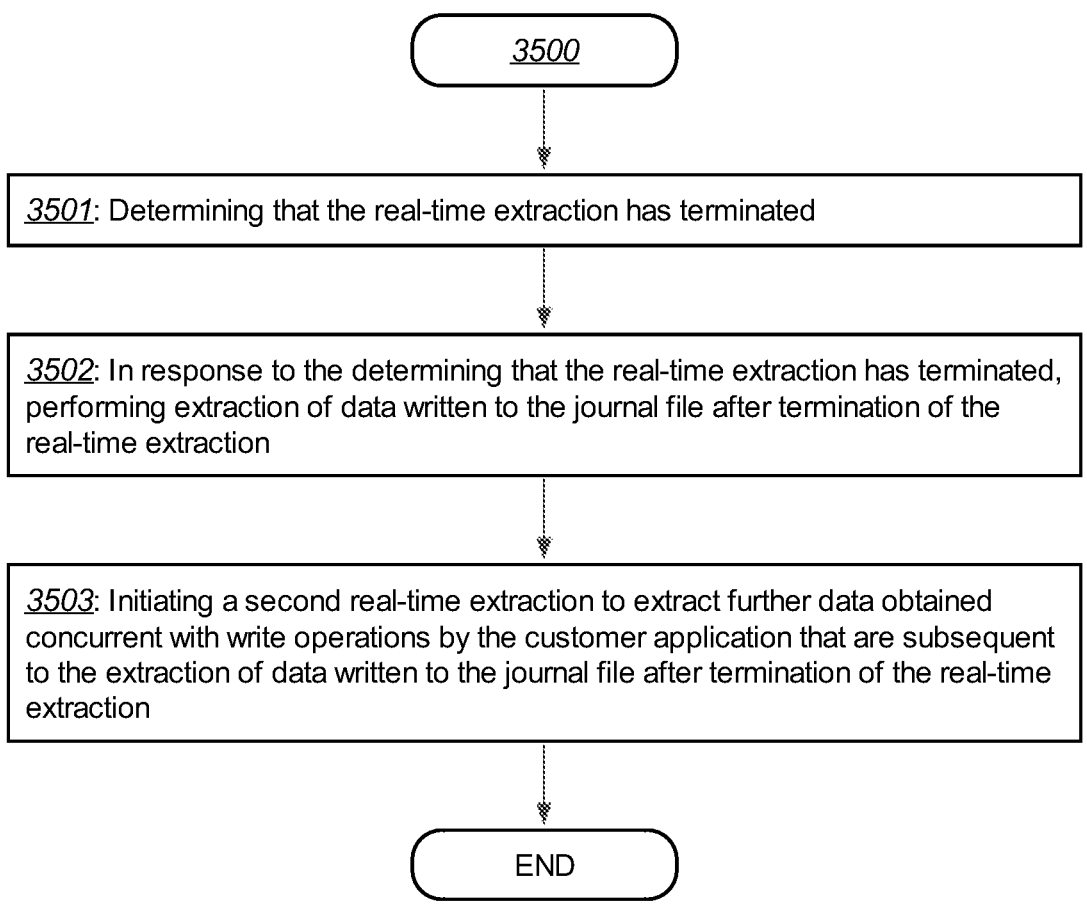

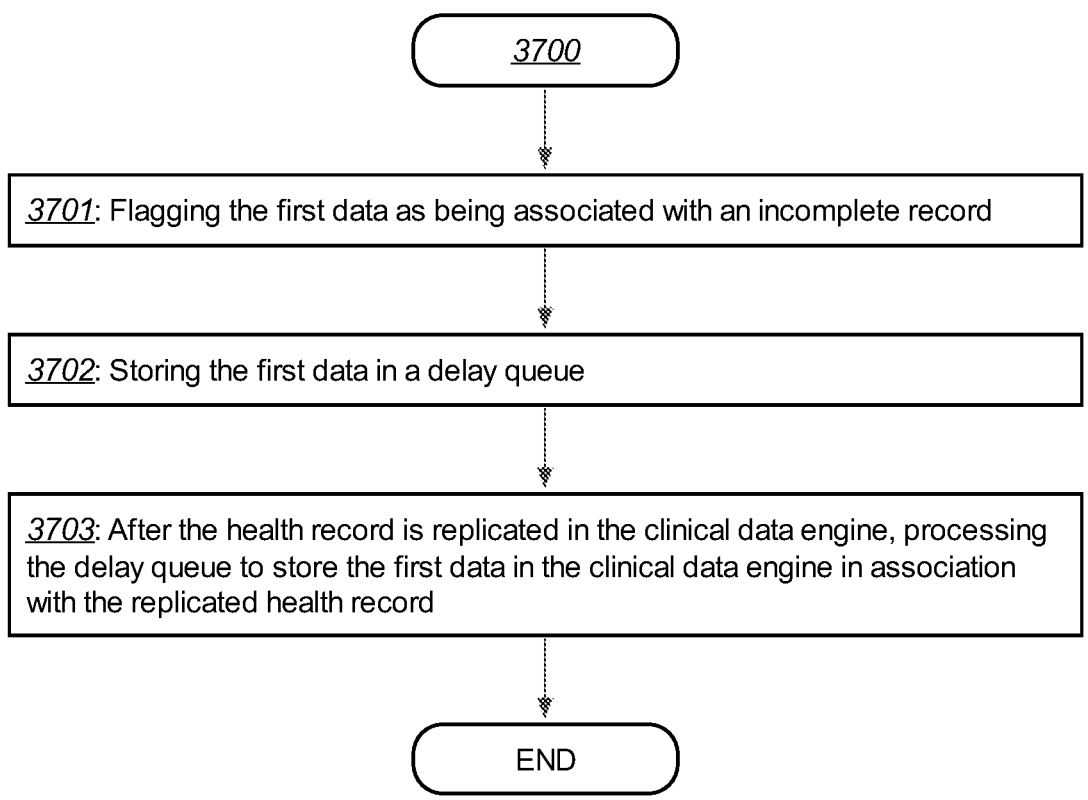

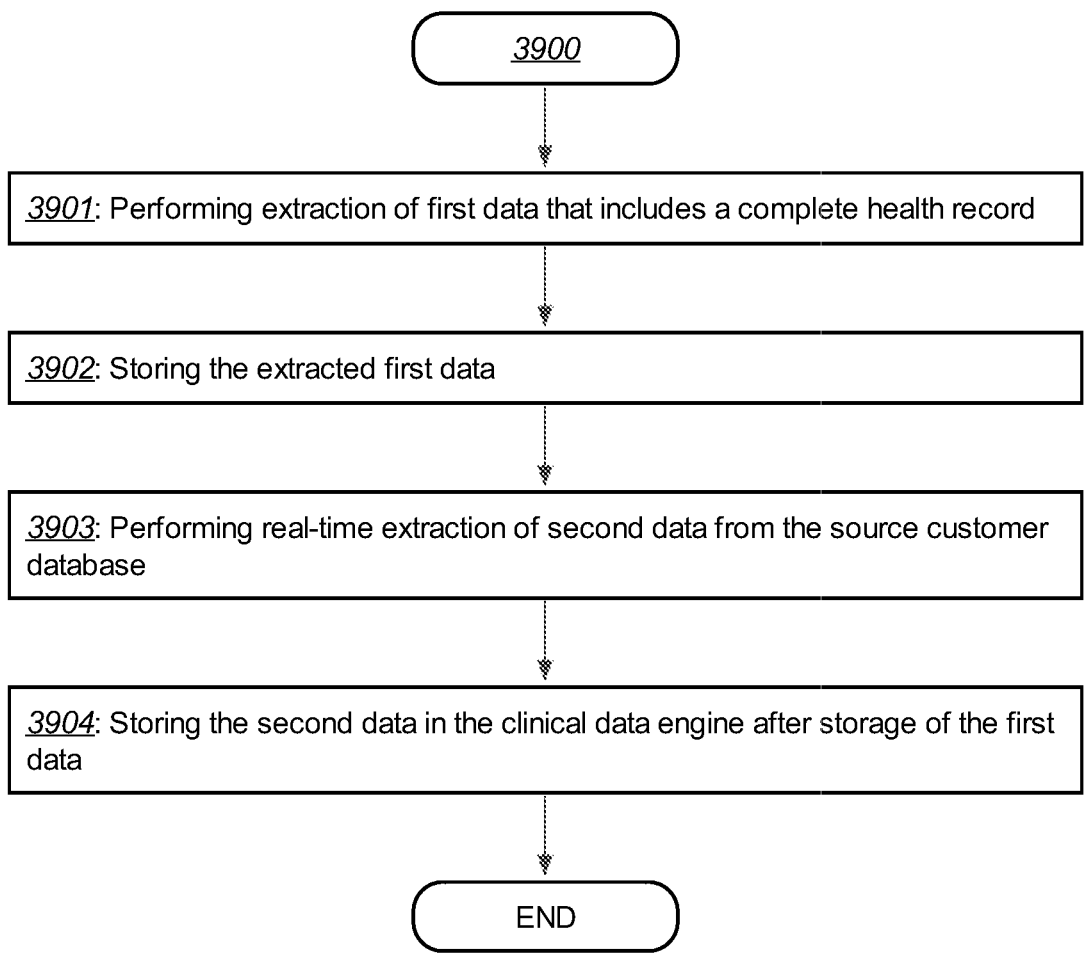

US 10,892,046 B1

SYSTEMS AND METHODS FOR DYNAMICALLY EXTRACTING ELECTRONIC HEALTH RECORDS

PRIORITY CLAIM

This application is a continuation-in-part of U.S. patent application Ser. No. 14/463,542, filed Aug. 19, 2014. This application claims priority to U.S. Provisional Patent Application No. 62/039,059, filed Aug. 19, 2014.

TECHNICAL FIELD

The present disclosure relates to methods, techniques, and systems for dynamically extracting electronic health record data from a source customer database that represents health records in a hierarchical format, and storing the extracted data in a clinical data engine that represents the health records in a manner that logically preserves the hierarchical format while providing a relational access model to the health records.

BACKGROUND

Present day health care information systems suffer from a number of deficiencies. A core shortcoming relates to the preferred data representation model. Many prominent health care information systems represent electronic health records using a hierarchical database model, such as is provided by the MUMPS ("Massachusetts General Hospital Utility Multi-Programming System" or "Multi-User Multi-Programming System") programming language. MUMPS dates from the 1960s.

The MUMPS programming model provides a hierarchical, schema-free, key-value database. Hierarchical data models can be easy to understand and efficient to process, but can at the same time be inflexible in terms of data modeling, because they can only represent one-to-many relationships between data items.

The MUMPS hierarchical data model stands in contrast to the relational data model, first presented in 1970. (Codd, A Relational Model of Data for Large Shared Data Banks, Communications of the ACM, vol. 13:6, June, 1970.) The relational data model represents data as relations each defined as a set of n-tuples, typically organized as a table. Today, systems that use hierarchical data models have been largely displaced by relational database systems, such as those offered by Microsoft, Oracle, Sybase, IBM, Informix, in addition to various open source projects.

The market domination of relational database systems has yielded corresponding technological advances, including improved programming language support, improved management systems, better development environments, more support tools, and the like. Also, the relational database field benefits from a substantially larger community of skilled database programmers, analysts, and administrators.

Despite the advances of relational database systems, MUMPS is still widely used in some industries, including healthcare. The use of MUMPS presents the healthcare industry with a labor shortage, given the small existing community of skilled developers, system administrators and analysts. Moreover, it is difficult for healthcare organizations to implement or extend existing MUMPS-based systems, given the relatively rudimentary set of associated development environments, tools, interfaces, and the like. As a result, in many cases, healthcare organizations using MUMPS-based electronic health records cannot access their own data very easily, accurately, or efficiently.

In one stop-gap approach to addressing the problem of access to MUMPS-based data, some organizations choose to convert MUMPS-based data (e.g., health records) into relational data stored in commercial relational database systems such as those provided by ORACLE or Microsoft. Such conversion is typically performed via an Extract-Transform-Load ("ETL") process. ETL processes commonly run overnight and can take 24 hours or more before users can access the data, thereby delaying access to time-critical data. Also, many ETL processes map the incoming data to thousands of tables, resulting in a data model that is cumbersome to understand, use, or modify, even with modern tools and database management environments.

In sum, MUMPS-based electronic health records are largely inaccessible for development by modern-trained database developers, system administrators, and analysts. This inaccessibility results in reduced innovation, increased costs, poorer health outcomes, lower quality of service, and the like.

BRIEF DESCRIPTION OF THE DRAWINGS

FIGS. 3A-3K are flow diagrams of data extraction processes performed by example embodiments.

DETAILED DESCRIPTION

Figure 1:
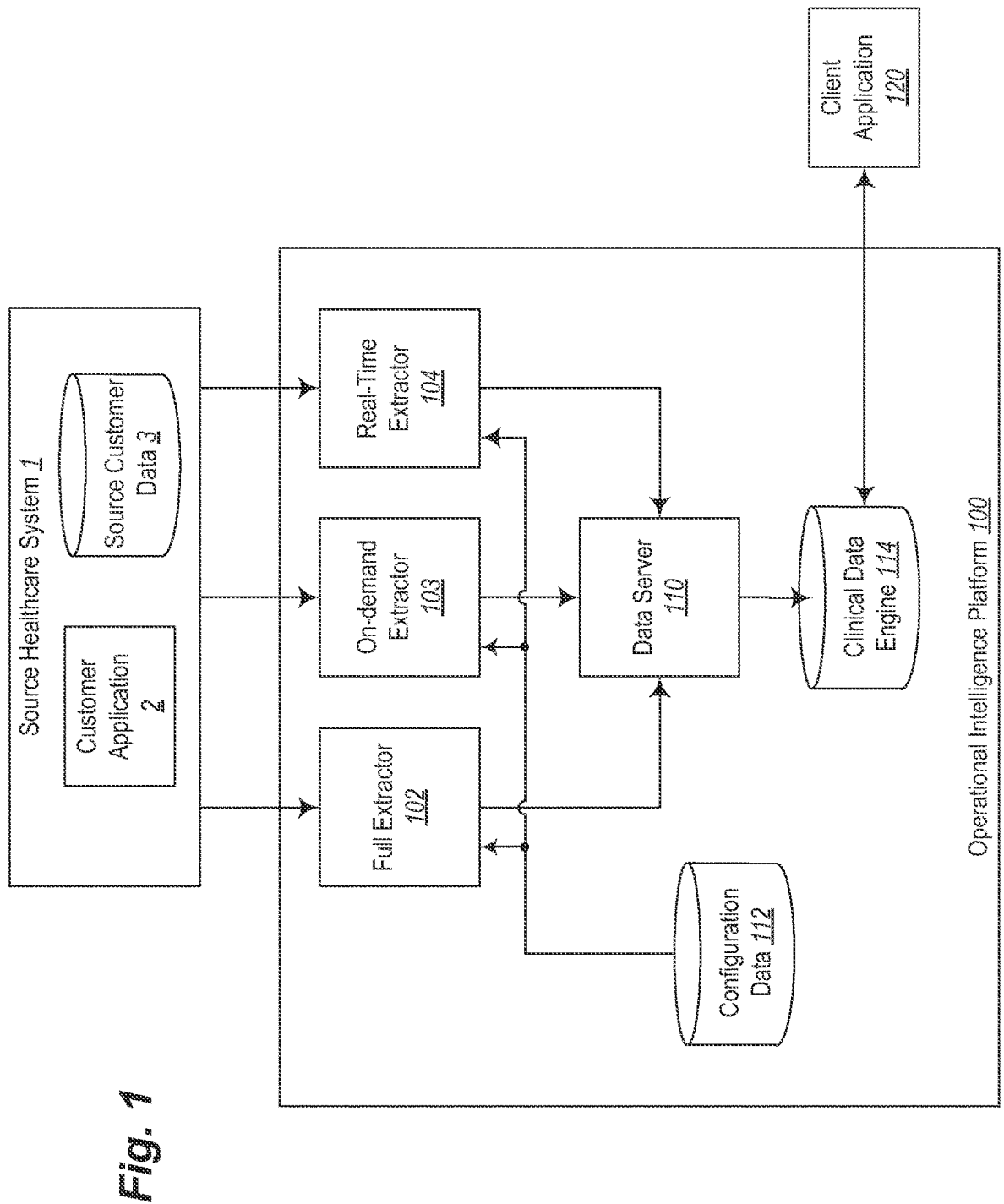
FIG. 1 is a block diagram of an operational intelligence platform according to an example embodiment.

Embodiments described herein provide enhanced computer- and network-based methods and systems for dynamically extracting and replicating electronic health records. Some embodiments provide an Operational Intelligence Platform ("OIP") that is configured to manage the extraction of electronic health records obtained from a source health care system. In some embodiments, the OIP is configured to extract electronic health record data from a source customer database that represents health records in a hierarchical format, such as a MUMPS-based representation. The OIP may then translate the extracted data into a relational representation that that logically preserves the hierarchical format. The OIP can then store the translated data in a database that provides relational access. The extraction and translation may occur in substantially real time, such that relational access can be provided to a live data image hosted by the OIP.

The OIP may also facilitate the development and/or operation of client modules or applications that access (e.g., obtain, present, modify) the electronic health records in a manner that is substantially or totally independent of the source health care system. For example, a client module of the OIP may be configured to present, query, report, and generate messages related to electronic health care data that is relevant to a particular patient and that is hosted by the OIP.

The described techniques address at least some of the above-described shortcomings with MUMPS-based electronic health records. In particular, the described techniques provide a mechanism by which modern programming paradigms and technologies can be applied to data hosted by an existing MUMPS-based system, such as by providing a relational access model or a dependency-free API ("Application Program Interface") for accessing the data. Such an API facilitates access to the data via any number of modern programming languages, thereby decoupling the data from its dependencies on the MUMPS language. The OIP is in effect capable of providing real-time, relational access to existing MUMPS-based electronic health records, while respecting and retaining (at least logically) the hierarchical nature of the original electronic health records. By providing relational access, the OIP facilitates and accelerates the development of new healthcare information systems, applications, or modules, as such can be developed by the larger community of skilled developers operating technologically advanced development tools associated with the relational database market.

The OIP in some embodiments facilitates real-time, dynamic, clinical analytics that deliver visibility and insight into health data, streaming events and clinical operations. The OIP may provide modules or services that allow users to run queries against streaming data feeds and event data to deliver real-time analytics and applications. The OIP may thus provide healthcare provider organizations the ability to make decisions and immediately act on these analytic insights, through manual or automated actions. In at least some embodiments, providing such functions via the OIP is based at least in part on the data extraction techniques described herein. Additional details regarding an example techniques for implementing an embodiment of an Operational Intelligence Platform are provided in U.S. Provisional Application No. 62/039,059, entitled "A DATA SYSTEM TO ENABLE HEALTHCARE OPERATIONAL INTELLIGENCE" and filed Aug. 19, 2014, the contents of which are incorporated herein by reference in its entirety.

1. Data Extraction in the Operational Intelligence Platform

FIG. 1 is a block diagram of an operational intelligence platform according to an example embodiment. More particularly, FIG. 1 shows an operational intelligence platform 100 extracting data obtained from a source healthcare system 1. The source healthcare system 1 includes a customer application 2 and source customer data 3. The customer application 2 may be, for example, a health records access and/or management application. In typical embodiments, the source customer data 3 represents electronic health records in a hierarchical data representation, such as may be provided by MUMPS or similar languages.

The illustrated operational intelligence platform 100 includes three distinct extractors 102-104, a data server 110, a configuration database 112, and a clinical data engine 114. While the modules of the platform 100 will be described in more detail below, the following provides an overview of their operation. The configuration database 112 includes data that directs the operation of the extractors 102-104, such as by specifying which health care records are to be extracted in a particular run. The data server 110 operates as an intake subsystem, and is responsible for receiving data updates from the extractors 102-104, and writing them to the clinical data engine 114. The clinical data engine 114 is responsible for storing and providing access to transformed MUMPS records obtained from the source healthcare system 1.

The extractors 102-104 (sometimes also referred to as "spigots") operate in concert to extract data from the source customer database 3. While FIGS. 2A-2C, below, describe specific techniques for extracting source customer data, the following discussion provides an overview of the functions performed by the extractors 102-104 in various embodiments. The full extractor 102 is a batch or bulk extractor that is configured to extract all or a specified collection of records from the source customer database 3 or a clone, mirror, or backup thereof (generally referred to as the "record source"). The real-time extractor 104 is configured to obtain data updates to the source customer database 3 as they occur in or about real time. The real-time extractor 104 may also or instead be configured to obtain information about data updates and/or application operations in or about real time. The real-time extractor 104 (or multiple distinct instances thereof) obtains information about events or operations performed with respect to the source customer applications (e.g., client programs used to manipulate patient records) and/or third-party applications (e.g., fitness monitoring applications, health tracking applications). Such events or operations may include user interface events (e.g., mouse clicks, button presses), application-level events/operations (e.g., open form, log in), data access events/operations (e.g., save preferences, modify record, delete file), or the like. The on-demand extractor 103 pulls data records that are associated with real-time updates but that are not already present in the clinical data engine 114. For example, if the real-time extractor 104 encounters an update to a patient record that does not exist in the clinical data engine 114, the on-demand extractor 103 will obtain the required record from the source customer data 3 or other record source and store it in the clinical data engine 114, so that it can be updated as necessary by the real-time extractor 104.

The records in the source customer data 3 which are consumed by the OIP 100 may be obtained from various sources and/or represented in different ways. For example, the records may be obtained directly from the a production server/database (e.g., a live database that is serving clinicians and patients), a report shadow database (e.g., a utility copy utility copy for running reports), a production shadow database (e.g., near live, service as a backup of production), and/or a production mirror database (e.g., live, service as a disaster recovery, fail-over instance of production data). In some embodiments, the source for the records of the source customer data 3 may be specified and/or determined automatically by rule and/or conditions (e.g., to use a shadow or mirror database at certain times of day or when traffic or load on the production database increases beyond a specified level). Thus, while records are herein discussed and shown as being obtained directly from the source customer data 3, it is understood that those records may in some embodiments be obtained from sources other than a live production database of the customer.

Typical embodiments initially perform a full extraction of the record source, in order to populate the clinical data engine 114 with all (or a specified subset) of the records present in the source customer data 3. To perform full extraction, the platform 100 employs the full extractor 102 to process a set of records from the record source. The set of records may be all of the records in the record source or some subset thereof, as may be specified by an initial input the configuration data 112. In some embodiments, the full extractor 102 obtains one record from the record source at a time. Other embodiments receive blocks of records from the record source. The full extractor 102 processes each record in no particular time order, and sends each as a message to the data server 110. Depending on the number and size of the records in the record source, the full extractor 102 can take a significant length of time (e.g., days or weeks) to complete. To speed up extraction and message sending throughput, multiple instances of the full extractor 102 can be run as concurrent processes or threads obtaining data from one or more record sources (e.g., production and shadow servers). In such a case, each full extractor 102 is allocated or assigned a distinct set of records to process.

During the full extraction process, real-time extraction is performed concurrently by the real-time extractor 104. To ensure that data extracted from the source customer data 3 is always current, the real-time extractor 104 is initiated before the full extractor 102. All updates to the source customer data 3 are captured by the real-time extractor 104 and thus, the extracted data, no matter how long the full extractor 102 takes to complete, will always be current. All extracted records will have been written to the source customer data 3 just prior to those records appearing in the real-time extractor 104. So long as the real-time extractor 104 is operating, an update to data in the source customer data 3 will always be reflected in the clinical data engine 114 within the operational latency (e.g., the amount of time it takes for an update to the source customer data 3 to be captured and written) of the real-time extractor 104. In some embodiments, the real-time extractor delays writing updates to the clinical data engine 114 until the full extractor has completely extracted the corresponding record.

The on-demand extractor 103 is responsible for filling in gaps in the clinical data engine 114 identified during operation of the real-time extractor 104. Given that the full extraction process can take an extended period of time to complete, and given that the real-time extractor 104 is creating and/or updating new records, there may gaps in data records stored in the clinical data engine 114. In particular, when the real-time extractor 104 initiates an update to a specified patient data record, the patient record may or may not be present in the clinical data engine 114, such as because the full extractor 102 has yet to process that record. When the record is present in the clinical data engine 114, the update to the record can be performed directly. On the other hand, when the record is absent from the clinical data engine 114, the record must be first fetched and stored by the on-demand extractor 103, so that the update can complete.

Some embodiments perform on-demand extraction by way of a delay queue (also sometimes referred to as an "update buffer"). First, given an update to a specified record, the clinical data engine 114 is queried to determine whether the record exists. Upon determining that the record does not exist, the update is flagged and placed in a delay queue associated with the record. The on-demand extractor 103 then extracts the record from the record source. Extracting the record can take some time, depending on the complexity of the record. In the context of electronic health records, for example, the record can comprise many sub-parts, including patient information, condition updates, chart entries, and the like.

Once the record has been populated to the clinical data engine 114, the delay queue can be processed. At this time, the delay queue may contain multiple updates, as additional updates may have been added (by the real-time extractor 104) to the queue during extraction of the record from the record source. In some cases, at least some of the queued updates may be duplicative of updates already performed or reflected by the extraction of the record. Thus, care may need to be taken to assure that those updates are either not performed, or that if they are performed, they will not result in an inconsistency between the source customer data 3 and the clinical data engine 114.

For example, the initial real-time update that caused the on-demand extractor 103 to fetch the patient data record will typically already be reflected in the patient record obtained by the on-demand extractor 103. Thus, this update (the oldest update in the delay queue) should not be performed unless doing so will not result in a data inconsistency.

Some embodiments may use time stamps to determine whether or not to perform updates in the delay queue. If updates in the delay queue are time stamped and each patient records includes an associated modification time, the delay queue may be processed by only performing updates that have time stamps that are later than the last modification time of the patient record.

The real-time extractor 104 is responsible for capturing real-time updates to the source customer data 3, and forwarding those updates for storage in the clinical data engine 110. Typically, the real-time extractor 104 is run as a process or similar unit of computation (e.g., thread) on a system that hosts the source customer data 3. For example, the real-time extractor 104 may be run as a process on a server that hosts a production, shadow, or mirror database that stores the source customer data 3.

In the illustrated embodiment, the real-time extractor 104 operates in two modes: primary and secondary. The purpose of the primary mode is for the real-time extractor to run continuously to copy new data in real time to the clinical data engine 114 and/or to the other data-consuming services of the platform 100. In primary mode, the real-time extractor 104 taps into data as it streams into one or more journals associated with the source customer data 3. In typical embodiments, as a customer application 2 writes data to the source customer data 3, the data is first stored in a journal file. The real-time extractor 104 copies data written to the journal file, converts it into a message, and forwards the message to the data server 110 for storage in the clinical data engine 114.

The purpose of the secondary mode of operation is to recover from interruptions to primary mode real-time extraction. After an interruption (e.g., due to machine failure, network outage), when the real-time extractor 104 resumes, it cannot resume in primary mode because all new incoming real-time data will be writing to an incomplete clinical data engine 114, due to updates missed during the interruption. Thus, in secondary mode, the real-time extractor performs a "catch up" operation. When the real-time extractor 104 resumes, it determines the last time an update was successfully made to the clinical data engine, and re-processes any journals that were created since that time. Then, the real-time extractor 104 processes a historical journal file data from the oldest non-processed data to the newest. In some cases, this may include processing multiple journal files, from oldest to newest. When the real-time extractor 104 completes processing all historical journal file data, the real-time extractor 104 ceases operation in secondary mode and proceeds operating in primary mode.

Journal files are files that are created in the source healthcare system 1 by the database management system hosting the source customer data 3. For example, a MUMPS database creates (or updates) journal files as its database is updated or otherwise modified. In some embodiments, each change to the database is written to the database and to a journal file. Journal files are typically created in chunks (e.g., 1 GB of data at a time) and written to disk using a sequential ordering scheme together with the implicit timestamp of the last write. Journal files that are processed by the secondary mode of the real-time extractor 104 are thus processed in time-based order, from oldest to newest.

Note that while the above techniques are described with respect to journal files, the techniques may be equally applicable in other architectures or with other types of journal files or data. For example, some database systems may create journal files in time-based chunks (e.g., every hour or day) rather than size-based chunks. In other cases, data may be recovered from a log file or other source that is not strictly used for journaling purposes.

The above-described extraction processes can be configured in various ways, typically by way of settings or other data specified in the configuration data 112. The configuration data 112 may specify the records that are to be extracted by full extraction; how many processes to dedicate to each of the different extractors 102-104; which machines to use for execution, data sources, data destinations, and the like. Typically, the extractors 102-104 consult the configuration data 112 upon startup, although configuration data may also or instead be transmitted to the extractors 102-104 at any time during their execution.

Configuration data 112 may specify a set of records to extract. For example, suppose that the source customer data 3 includes three records, identified as A, B, and C, and the configuration data 112 specifies records A and C are to be extracted. In this case, the full extractor 102 will process only records A and C. The real-time extractor 104 will also be configured to capture only updates to records A and C. Given this example set of data, the on-demand extractor 103 will never encounter record B (even in face of updates to that record), as the on-demand extractor 103 will be only invoked in service of the real-time extractor 104 due to updates to records A and C.

Configuration data 112 may also specify a time-constrained extraction. In this model of extraction, the configuration data 112 specifies a time range (e.g., the last 10 days, last year) for which records are to be extracted. For example, the configuration data 112 may specify that the full extractor 104 should only extract records created (e.g., new patient records) during the last month.

The data server 110 functions as an intake subsystem, and is responsible for receiving data updates from the extractors 102-104, and writing them to the clinical data engine 114. The data server 110 receives messages from the extractors 102-104. The received messages include data from the source customer data 3. In response to the received messages, the data server 110 determines whether and what types of additional processing or translation is required, and then performs a corresponding storage operation in the clinical data engine 114. The data server 110 also includes synchronization and timing logic to assure that updates are performed in correct order. For example, the data server 110 may manage a queue that serves to delay updates to records that are not yet present in the clinical data engine 114.

In some embodiments, the platform 100 supports two distinct types of initiation (e.g., initial population) of the clinical data engine 114: incremental initiation and complete initiation. Both types of initiation begin with a new, empty clinical data engine 114 and terminate when all records (or all records specified by the configuration data 112) in the source customer data 3 have been replicated to the clinical data engine 114.

In incremental initiation, the real-time extractor 104 is first initiated. The real-time extractor 104 then begins transmitting messages reflecting updates to the data server 104, which stores the updates in the clinical data engine 114. After initiation of the real-time extractor 104, the full extractor 102 is initiated. As the real-time extractor 104 processes, the on-demand extractor 103 serves to populate the clinical data engine 104 with absent records referenced by updates received by the real-time extractor 104. When the full extractor 102 completes processing all of the records in the source customer data 3, the full extractor 102 and the on-demand extractor 103 may be terminated. Note that if the full extractor 102 was configured to only extract a subset of the records in the source customer data 3, the on-demand extractor 103 may continue executing because it may need to fetch records that were not part of the specified subset obtained by the full extractor 102.

In complete initiation, the real-time extractor 104 is first initiated. The real-time extractor 104 then begins transmitting messages reflecting updates to the data server 104, which stores the updates in the clinical data engine 114. After initiation of the real-time extractor 104, the full extractor 102 is initiated. When the full extractor 102 and the real-time extractor are time aligned (e.g., processing data updates having the same timestamp or having timestamps that are within a specified window of each other), the process is complete, and the clinical data engine is ready to use. At this time, the full extractor 102 may be terminated. Note that the on-demand extractor 103 need not be used in this model of initiation, because all records will eventually be fetched by the full extractor 102. However, if the on-demand extractor is not used, the clinical data engine 114 may contain inconsistent data (and thus not be usable) until completion of the full extraction. Other embodiments will employ the on-demand extractor 103 in order to assure a higher level of (or more rapidly achieved) data consistency between the source customer data 3 and the clinical data engine 114.

The clinical data engine 114 includes data extracted from the source customer data 3. The clinical data engine 114 may include distinct databases. For example, a first database may be a scalable, highly available database that is used to store the data obtained by the extractors, possibly using a Log Structured Merge Tree format, as described below. A second database may be an ontology database that represents the concepts of the particular deployment, such as the types of activities, actions, users, and contexts that can occur in the healthcare setting. A third database may store a clinical activity network, which is a semantic network that represents the activities that are themselves represented by data items stored in the first database and/or the source customer data. For example, the semantic network may represent an activity such as a patient bed change that is represented by two distinct updates to a patient record. As another example, the semantic network may represent an activity such as a drug administration, which is represented by multiple distinct updates to the patient record (e.g., a drug prescription entry, a drug acquisition entry, a drug administration entry). The semantic network typically also associates activities with time, thereby imposing a time ordering on activities, something which is not present in source customer data itself, because the source customer data typically provides only a "present time" snapshot of the state of a patient record and related data. By using these techniques, the system can represent, track, and analyze logical activities that map to one or more actual clinical actions and events that are represented in the source customer data, even though the source customer data does not by itself represent the activity and rather only represents the ground-level facts as data updates to a patient record.

The extraction techniques described herein provide a number of benefits. First, there is no need to stop or lock an in-production instance of a server or other system that hosts the source customer data 3. Also, the customer need not provision additional computing systems, as the platform 100 executes substantially or entirely on a system that is independent of the source healthcare system 1. In addition, the customer need not provide additional support personnel to manage or facilitate the extraction process. Further, the platform is tolerant of intermittent system failures or outages on part of the source healthcare system 1. Also, the extraction process does not disrupt normal operation of the source healthcare system 1.

Although the techniques are primarily described in the context of healthcare systems, the techniques are equally applicable to other business contexts, such as banking, inventory systems, customer relationship management systems, human resources systems, or the like.

Also, the described techniques may be employed in contexts that do not provide a relational access model to health records or other data that is initially represented in a hierarchical data format. For example, some embodiments extract data from flat or relational data sources in order to use the data in other ways, such as storing the data in another format (e.g., a hierarchical format), filtering the data, incorporating the data into a semantic network or other knowledge representation framework, or the like.

Note also that although the platform 100 is described as having a specific set of modules, other embodiments may decompose the functionality of the platform 100 in other ways. For example, rather than using a distinct on-demand extractor 103, another embodiment may integrate the functions of the on-demand extractor 103 into the real-time extractor 104.

2. Example Data Extraction Data Flows

Figure 2A:
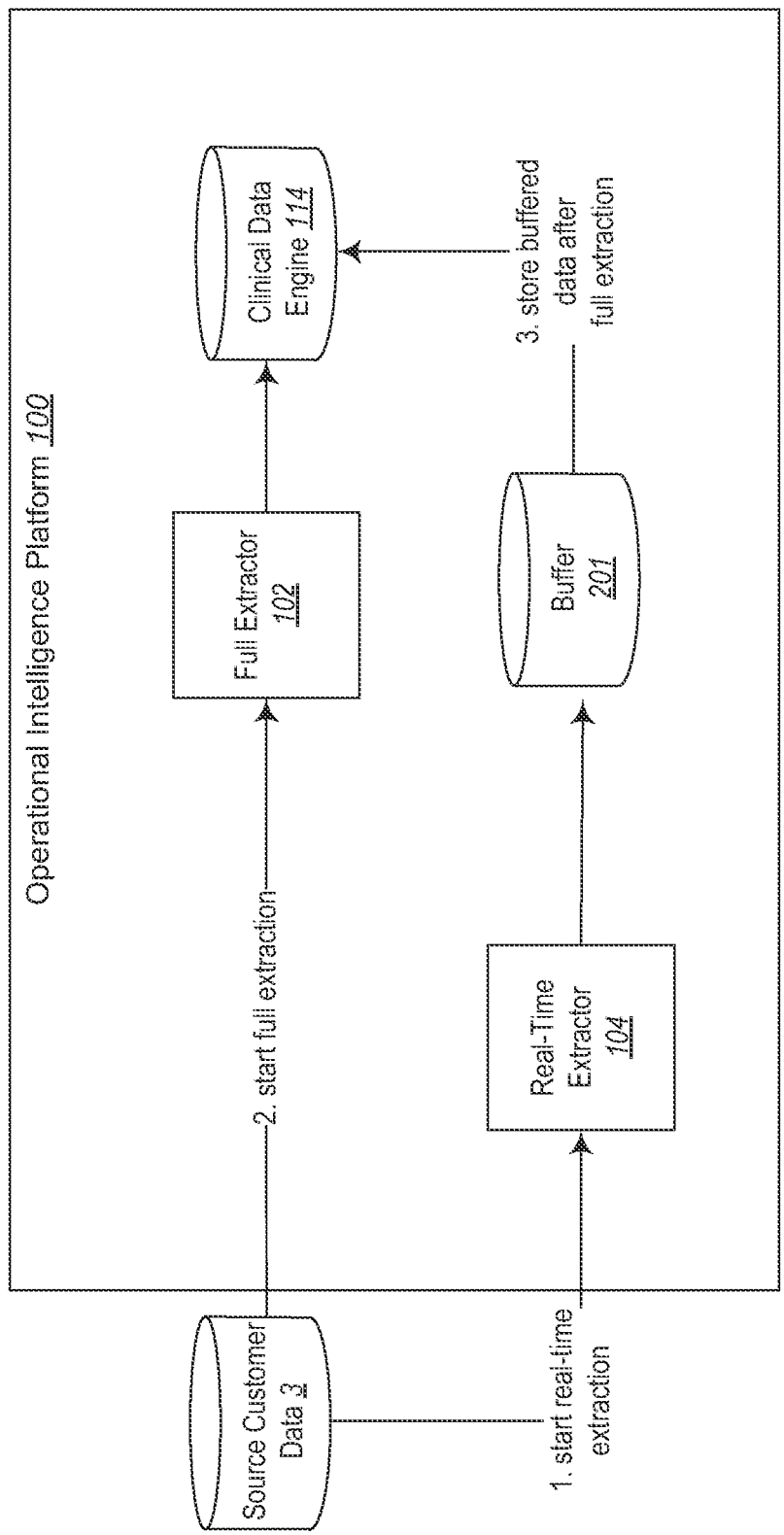
FIGS. 2A-2C are block diagrams illustrating extraction data flows according to example embodiments.
Figure 2B:
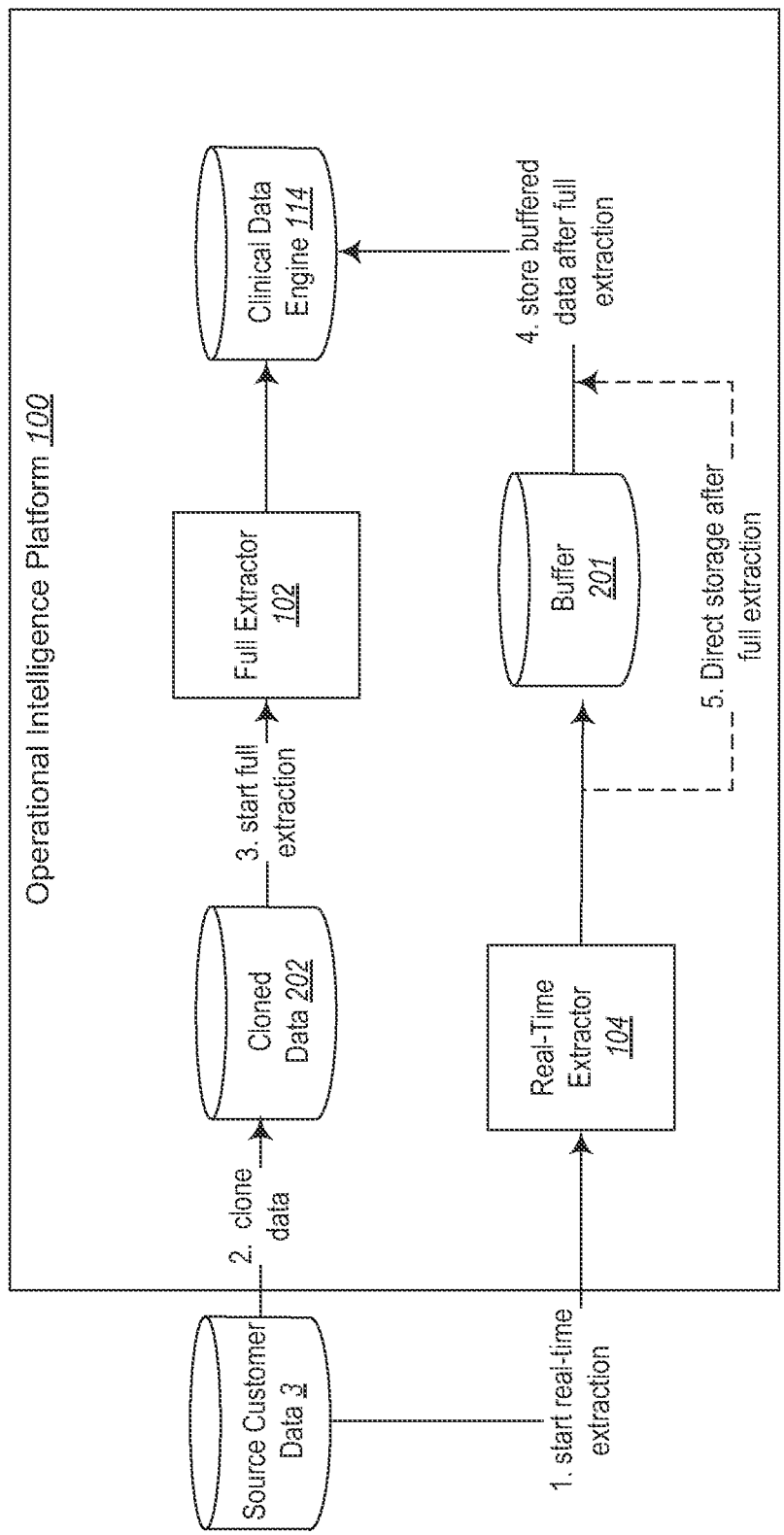
Figure 2C:
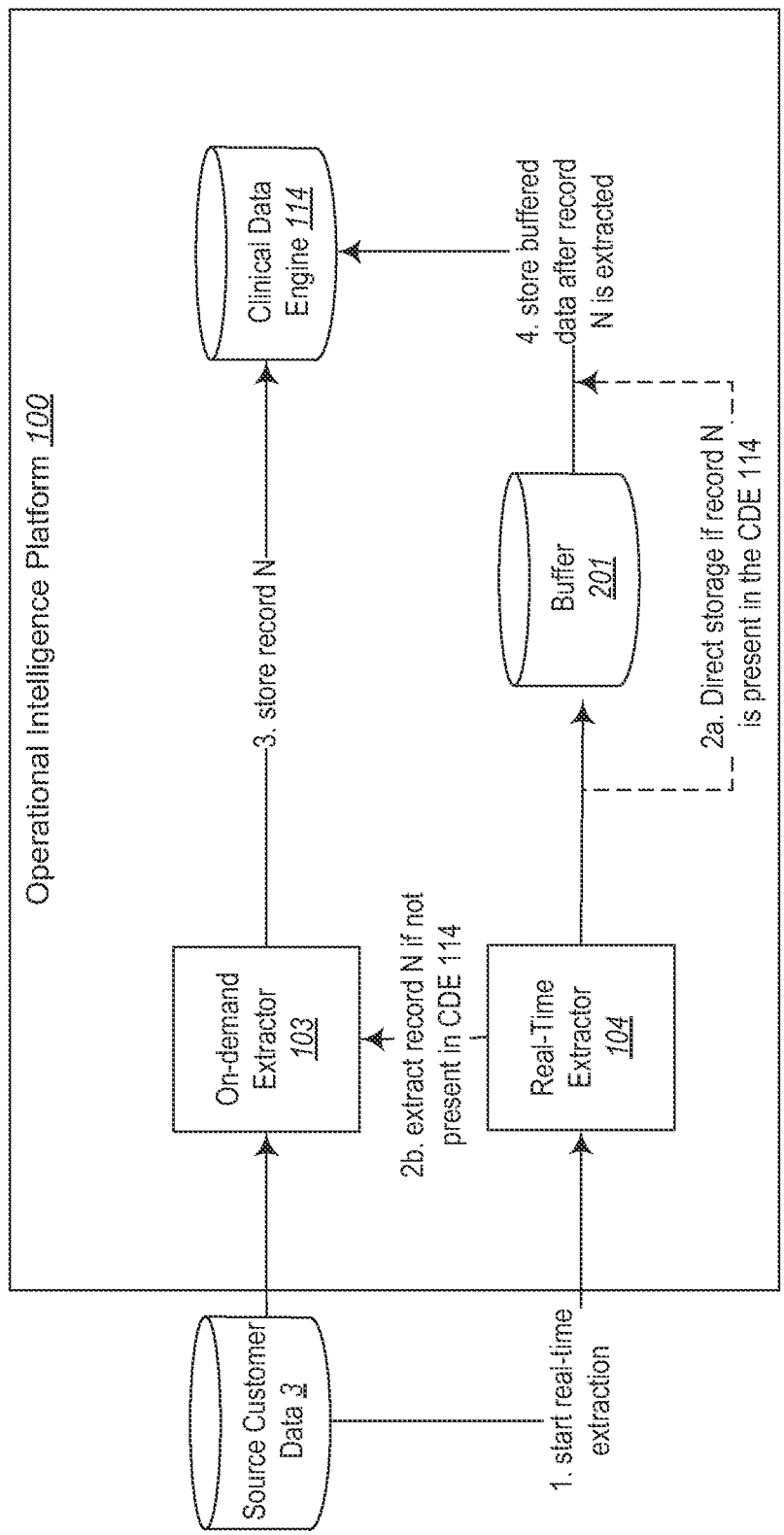

FIGS. 2A-2C are block diagrams illustrating extraction processes and data flows according to example embodiments. In particular, each of FIGS. 2A-2C illustrates a distinct approach to extracting and replicating electronic health records. The illustrated approaches are designed to address different customer and/or technical requirements presented in various deployment scenarios. Each of FIGS. 2A-2C depicts the extraction of electronic health records from the source customer data 3 to the clinical data engine 114 by the OIP 100. In typical deployments, the source customer data 3 contains several terabytes of data, meaning that a full extraction may take days or even weeks to complete. Also, in some deployments, the customer does not permit the OIP 100 to execute processes or other code modules on computing systems administered by the customer. For these and other reasons outlined below, the extraction processes of the OIP 100 must be configured and ordered to assure (at least at completion of the extraction process) that the data in the clinical data engine 114 is consistent with that stored in the source customer data 3.

FIG. 2A illustrates a first technique for extracting and replicating electronic health records. In FIG. 2A, the full extractor 102 is permitted by the customer to access the source customer data 3, such as by directly querying the source customer data 3 or some replication or clone thereof that exists on systems administered by the customer.

In the process of FIG. 2A, the OIP 100 first initiates execution of the real-time extractor 104. The real-time extractor 104 typically obtains updates from a journal file of the source customer data 3. As noted above, some deployments append every update to the source customer data 3 to a journal file. The real-time extractor 104 processes updates by monitoring the journal file, obtaining new updates appended to the journal file, and then storing the obtained updates in a buffer 201 managed by the OIP 100. The buffer 201 operates as a delay queue and may be implemented in various ways, such as by a database, log file, journal file, in-memory data structure (e.g., queue), or the like.

The OIP 100 next initiates the full extractor 102. The full extractor 102 processes all of the records of the source customer data 3 and stores data corresponding thereto in the clinical data engine 114. This process may take a substantial length of time (e.g., hours, days, weeks), during which the customer application 2 may update records in the source customer data 3 which have already been extracted to the clinical data engine 114. Such updates will, however, be captured by the real-time extractor 104 and stored in the buffer 201. For example, at a first time, the full extractor 102 extracts a record for patient X from source customer data 3. At a second time subsequent to the first time, the record for patient X is updated to reflect a changed blood pressure measurement. This update is captured by the real-time extractor 104 and is recorded in the buffer 201.

After the full extractor 102 has processed all of the records of the source customer data 3, the updates recorded in the buffer 201 are stored in the clinical data engine. This operation assures that updates made to patient records subsequent to their extraction to the clinical data engine 114 are also reflected in the clinical data engine 114, thereby assuring consistency between the source customer data 3 and the clinical data engine 114. To continue the above example, after completion of the full extractor 102, the blood pressure update to the record of patient X (that was recorded in the buffer 201) is stored in the clinical data engine 114, thereby making the record for patient X in the clinical data engine 114 consistent with the corresponding record in the source customer data 3.

Note that real-time extractor 104 continues to execute after the full extractor 102 terminates, and after the buffered updates are stored in the clinical data engine 114. Updates captured by the real-time extractor 104 subsequent to termination of the full extractor 102 may continue to be placed in the buffer 201 (from where they are directly stored in the data engine 114). Alternatively, the updates may be directly stored by the real-time extractor 104 in the data engine 114, thereby bypassing the buffer 201.

FIG. 2B illustrates a second technique for extracting and replicating electronic health records. In FIG. 2B, the customer has imposed a requirement that the OIP not burden the source customer data 3, such as by performing full extraction directly on, from, or involving a computing system that hosts the source customer data 3.

In the process of FIG. 2B, the OIP 100 first initiates execution of the real-time extractor 104. The real-time extractor 104 operates as discussed with respect to FIG. 2A, above, by buffering updates to the source customer data 3 in the buffer 201.

The OIP 100 next clones the source customer data 3 to cloned data 202. The cloned data 202 is a copy of the source customer data 3 that is hosted by the OIP 100. The cloned data 202 may in some embodiments be a backup of the source customer data 3, such as the most recent full backup created by the customer. By hosting the cloned data 202 local (e.g., on the same machine or local network) to the OIP 100, the OIP 100 need not run any special purpose code modules on computing systems administered by the OIP 100. In addition, the utilization of customer computing and/or network resources by or on behalf of the OIP 100 may be minimized.

Next, the OIP 100 initiates the full extractor 102. The full extractor 102 operates as discussed with respect to FIG. 2A, except that its data source is the cloned data 202 instead of the source customer data 3. The cloned data (e.g., a backup of the source customer data 3) may be represented as a collection of binary data files that each represent a subset of the records of the source customer data 3. When the files are configured to each represent complete records, the files may be processed in parallel, such as by launching multiple instances of the full extractor 102. Also, since the processed files may vary considerably in size (e.g., some files are a few megabytes in size while others are many gigabytes in size), large files may themselves be processed in parallel, where each extraction process or thread processes a specified range of records contained within the file. The described parallel processing techniques, facilitated by clone-based extraction, can result in significant speed-ups accompanied by data consumption rates higher than would be tolerated by direct access to the source customer data 3.

Once the full extractor 102 has completed, the updates stored in the buffer 201 by the real-time extractor 104 are stored in the clinical data engine 114, thereby making the clinical data engine 114 consistent with the source customer data 3. After the initial replication is complete, the real-time extractor 104 continues to execute in order to maintain ongoing consistency between the clinical data engine 114 and the customer data 3.

FIG. 2C illustrates a third technique for extracting and replicating electronic health records. By way of overview, the process of FIG. 2C differs from those of FIGS. 2A and 2B, in that the process of FIG. 2C facilitates early utilization of the clinical data engine 114 and related facilities of the OIP 100 without the need to complete a full extraction. The illustrated process does so by "lazily" extracting data from the source customer data 3 on an as-needed basis.

In the process of FIG. 2C, the OIP 100 first initiates execution of the real-time extractor 104. For a given update captured by the real-time extractor 104, the extractor 104 determines whether the corresponding record is already present in the clinical data engine 114. If so, the real-time extractor 104 directly stores the update to the clinical data engine 114. If not, the real-time extractor 104 causes the on-demand extractor 103 to obtain the record from the source customer data 3 and extract the record to the clinical data engine 114. During extraction of the record, the real-time extractor 104 may store the update that triggered the on-demand extraction (and possible additional updates to the record) in the buffer 201. Upon extraction of the record, updates corresponding to the record and stored in the buffer 201 are flushed to the clinical data engine 114.

In FIG. 2C, the extractors 103 and 103 cooperate in order to populate the clinical data engine 114 in an on-demand manner, based on updates that are made to the source customer data 3. Note that the on-demand population may be based on other or additional factors. For example, a client application of the OIP 100 may issue a query (e.g., for patient data), that causes the on-demand extractor 103 to extract a corresponding patient record from the source customer data 3. As another example, the on-demand extractor 103 may be provided an initial set of records to obtain, so that the clinical data engine 114 can be quickly "seeded" with data, such as to facilitate a study of some subset of the patients in a hospital (e.g., only patients who are currently admitted to the hospital, a random subset of patients, patients in a particular service).

The buffer 201 show in FIGS. 2A-2C may be processed in various ways. In the context of full extraction (e.g., FIGS. 2A and 2B), the buffer 201 may accumulate updates until termination of the full extraction process. However, the buffer 201 may be processed prior to the termination of full extraction in order to reduce storage requirements. For example, the buffer may be processed every hour (or when the buffer reaches a certain size or number of entries) to identify updates that correspond to records that have been extracted to the clinical data engine 114. The identified updates may then be written to the clinical data engine 114. In the context of on-demand extraction (FIG. 2C), the on-demand extractor 103 typically notifies the real-time extractor 104 or some other module that can selectively flush corresponding updates from the buffer 201 to the clinical data engine 114.

3. Example Data Extraction Processes

FIGS. 3A-3K are flow diagrams of data extraction processes performed by example embodiments.

Figure 3A:
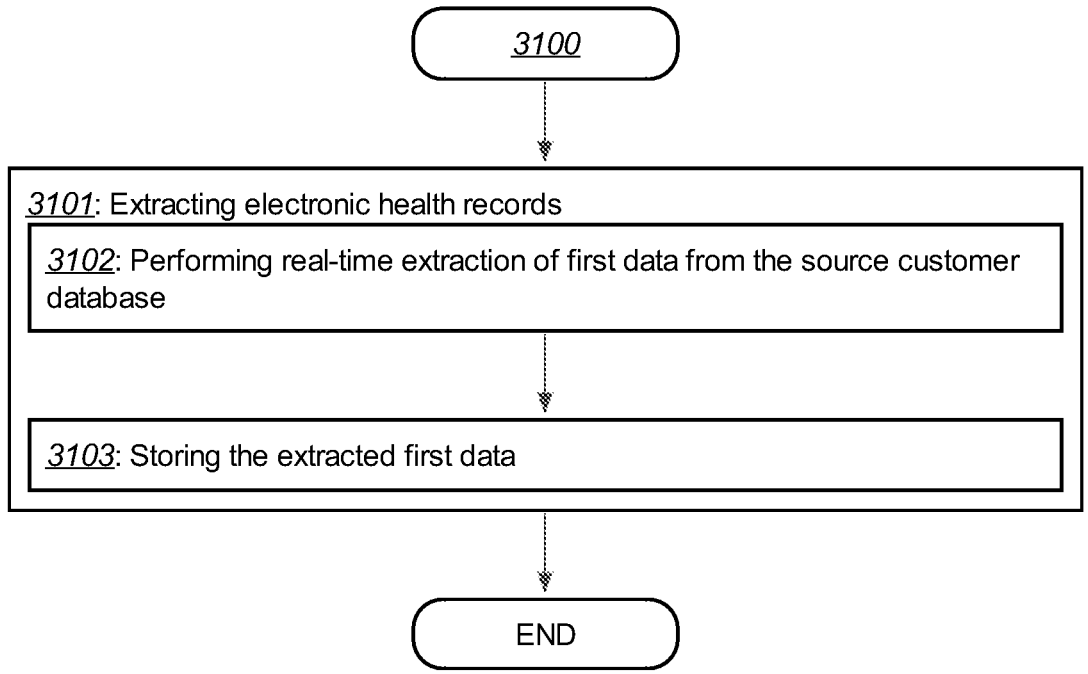

FIG. 3A is a flow diagram of example logic for replicating electronic health records. The illustrated logic in this and the following flow diagrams may be performed by, for example, one or more modules of the Operational Intelligence Platform 100 described with respect to FIGS. 1 and 2A-2C, above. More particularly, FIG. 3A illustrates a process 3100 that includes the following block(s).

Block 3101 includes extracting electronic health records from a source customer database that contains multiple electronic health records that are represented in a hierarchical data format, by: performing block(s) 3102 and 3103, described below. The process functions to establish and maintain consistency between the source customer database and a clinical data engine hosted by the platform 100. In some embodiments, the source customer database is a MUMPS database that represents health records, such as patient records, in a hierarchical data format. The source customer database is typically a live database that is being accessed and modified by customer applications, such as patient management systems.

Block 3102 includes performing real-time extraction of first data from the source customer database, wherein the first data is obtained from a journal file that includes updates to the source customer database that are based on write operations performed by a customer application to store the first data in the source customer database, and wherein the first data is obtained concurrent with the write operations performed by the customer application. As the customer application stores data into the source customer database, the data is also stored in an associated journal file. An example update could be an update to a patient's record reflecting a recent blood pressure measurement. The described process concurrently accesses the journal file to capture the first data in substantially real time. The process may obtain data from the journal file by periodically polling the file for changes, registering for events or other notifications of changes to the journal file, or by other inter-process communication mechanisms, such as pipes or tees.

Block 3103 includes storing the extracted first data in a clinical data engine that represents at least some of the multiple electronic health records in a manner that logically preserves the hierarchical data format while providing a relational access model to the health records. The clinical data engine is hosted by the platform 100, and provides relational access to patient records obtained from the source customer database. For example, the clinical data engine may represent the hierarchical records as one or more tables, and provide a SQL or related query interface to accessing those tables.

Figure 3B:
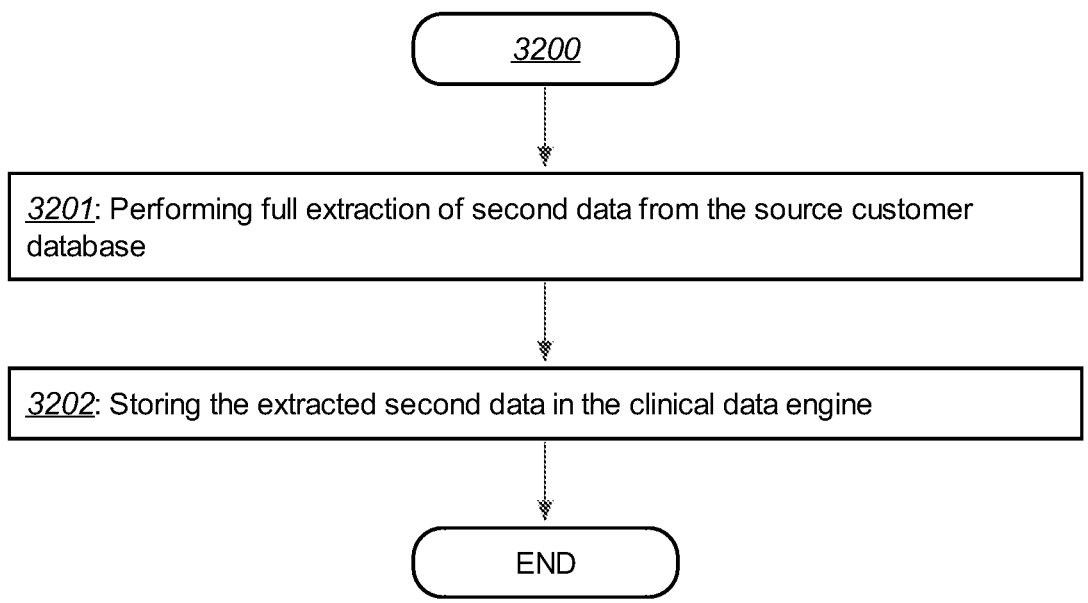

FIG. 3B is a flow diagram of example logic illustrating an extension of process 3100 of FIG. 3A. More particularly, FIG. 3B illustrates a process 3200 that includes the process 3100, wherein the extracting electronic health records includes the following block(s).

Block 3201 includes performing full extraction of second data from the source customer database, wherein the second data was written to the source customer database prior to initiation of the real-time extraction. In some embodiments, full extraction and real-time extraction are performed concurrently in order to respectively replicate previously written (historical) data and real-time updates. The full extraction processes all (or a specified subset) of existing health records in the source customer database.

Block 3202 includes storing the extracted second data in the clinical data engine. As discussed above, the data may be stored in a translated manner that retains the logical hierarchical nature of the data, while providing a relational access model to the data.

FIG. 3C is a flow diagram of example logic illustrating an extension of process 3200 of FIG. 3B. More particularly, FIG. 3C illustrates a process 3300 that includes the process 3200, wherein the extracting electronic health records includes the following block(s).

Block 3301 includes initiating the performing real-time extraction of first data from the source customer database prior to the performing full extraction of second data from the source customer database, so that any data written to the source customer database after the onset of the real-time extraction will be captured by the real-time extraction, while data that was written to the source customer database prior to the initiating the performing real-time extraction of first data from the source customer database will be processed by the full extraction. As noted, in at least some circumstances, it may be necessary to initiate the real-time extraction prior to the full extraction, so that no data updates occurring after the onset of the full extraction are missed. For example, if a blood pressure measurement for a particular patient is updated after that patient record is extracted by full extraction, that updated measurement will not be consistently represented in the clinical data engine if not captured by the real-time extraction.

Figure 3D:
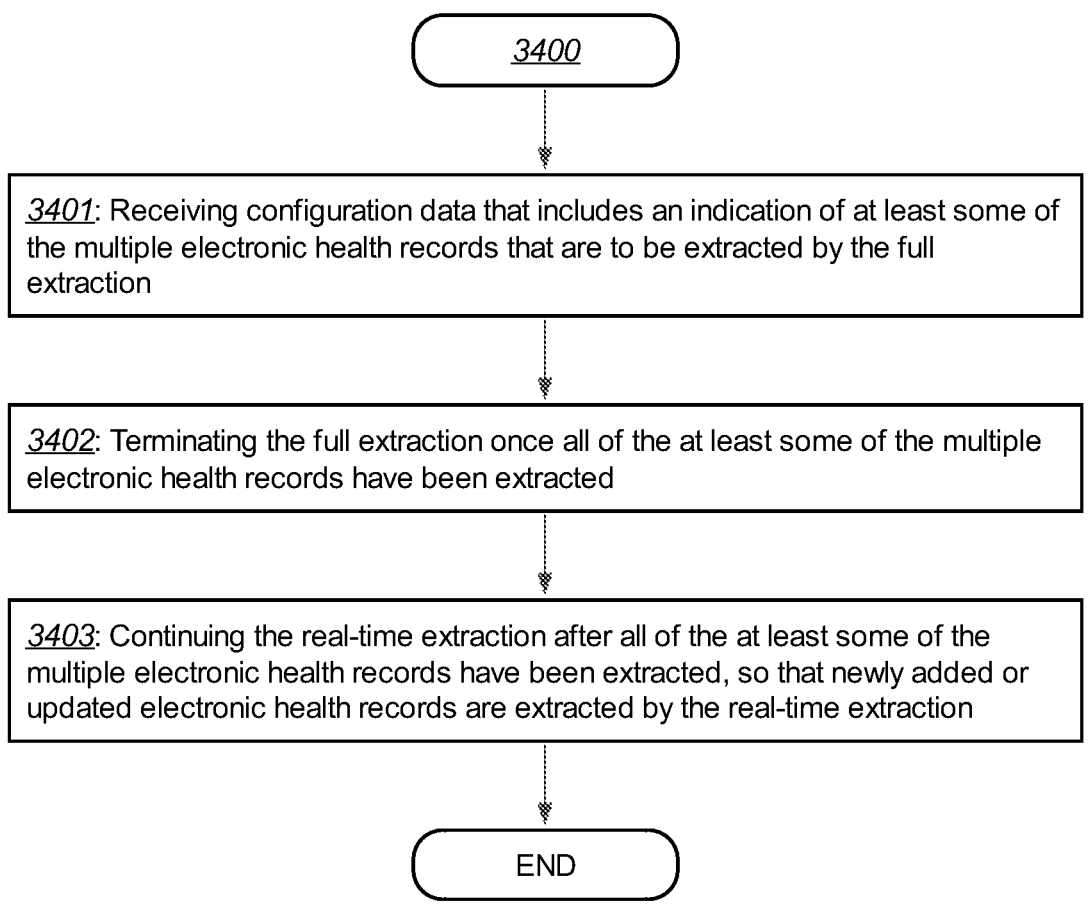

FIG. 3D is a flow diagram of example logic illustrating an extension of process 3200 of FIG. 3B. More particularly, FIG. 3D illustrates a process 3400 that includes the process 3200, wherein the extracting electronic health records includes the following block(s).

Block 3401 includes receiving configuration data that includes an indication of at least some of the multiple electronic health records that are to be extracted by the full extraction. The configuration data may be received from the configuration data 112, which may be a file, a database, specified via a user interface, or the like. In the healthcare context, records may be specified by patient identifiers or other globally unique identifiers. In some embodiments, the records may be specified on a time-based manner, such as those created or modified during a particular time period (e.g., last week, a specified year).

Block 3402 includes terminating the full extraction once all of the at least some of the multiple electronic health records have been extracted. Upon completion of the batch of records processing by the full extraction, the full extraction is typically terminated. In some embodiments, the full extraction may sleep or otherwise be suspended, such as to await a renewed batch of patient records to import.

Block 3403 includes continuing the real-time extraction after all of the at least some of the multiple electronic health records have been extracted, so that newly added or updated electronic health records are extracted by the real-time extraction. The real-time extraction continues executing in order to maintain consistency between the source customer database and the clinical data engine.

FIG. 3E is a flow diagram of example logic illustrating an extension of process 3200 of FIG. 3B. More particularly, FIG. 3E illustrates a process 3500 that includes the process 3200, wherein the extracting electronic health records includes the following block(s).

Block 3501 includes determining that the real-time extraction has terminated during the full-extraction. Real-time extraction may terminate for various reasons such as system failure, network failure, operator error, or the like. In some embodiments, the determination that real-time extraction has terminated may be automatic, such as by way of a watchdog service, a heartbeat monitor, exit codes, or the like.

Block 3502 includes in response to the determining that the real-time extraction has terminated, performing extraction of data written to the journal file after termination of the real-time extraction. When real-time extraction terminates, the data written to journal files after termination is processed in order to "catch up" to present time.

Block 3503 includes initiating a second real-time extraction to extract further data obtained concurrent with write operations by the customer application that are subsequent to the extraction of data written to the journal file after termination of the real-time extraction. The process may determine that the "catch up" extraction is complete in various ways, such as when all records in the journal file have been processed or by comparing timestamps in the journal to the current time. Note that the termination of the catch-up extraction will typically need to be synchronized with the re-initiation of real-time extraction, such as by restarting real-time extraction, noting the time stamp or other identifier of its first processed update, and then continuing the catch-up extraction until that time stamp or identifier is encountered, thereby guaranteeing that no updates are missed during the startup latency of the real-time extraction.

Figure 3F:
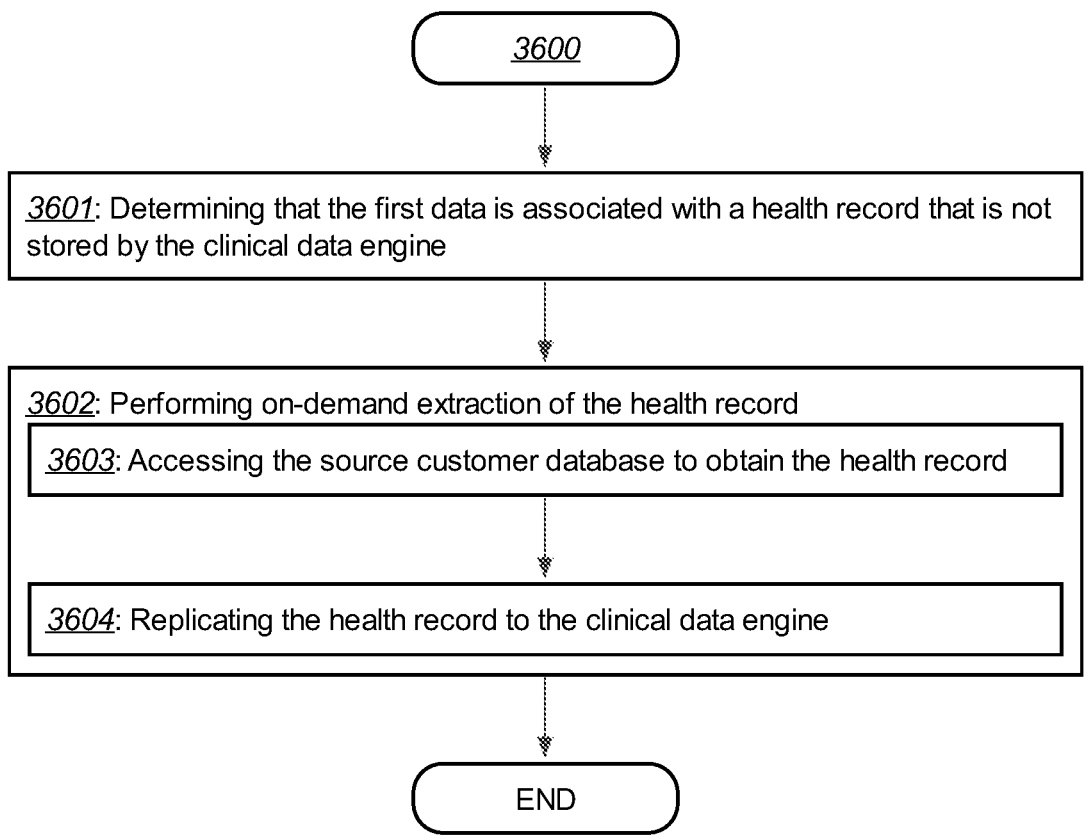

FIG. 3F is a flow diagram of example logic illustrating an extension of process 3100 of FIG. 3A. More particularly, FIG. 3F illustrates a process 3600 that includes the process 3100, wherein the extracting electronic health records includes the following block(s).

Block 3601 includes determining that the first data is associated with a health record that is not stored by the clinical data engine. The process may also perform on-demand extraction to obtain data records that are not present in the clinical data engine, such as records that are referenced by updates captured by the real-time extraction.

Block 3602 includes in response to determining that the first data is associated with a health record that is not stored by the clinical data engine, performing on-demand extraction of the health record, by: performing block(s) 3603 and 3604, described below.

Block 3603 includes accessing the source customer database to obtain the health record. Accessing the source customer database will typically include making a query against the source customer database to fetch the health record in question.

Block 3604 includes replicating the health record to the clinical data engine. Replicating the health record typically includes storing the record and its associated data in a in the clinical data engine as described herein.

FIG. 3G is a flow diagram of example logic illustrating an extension of process 3600 of FIG. 3F. More particularly, FIG. 3G illustrates a process 3700 that includes the process 3600, wherein the performing on-demand extraction of the health record includes the following block(s).

Block 3701 includes flagging the first data as being associated with an incomplete record. As noted above, when real-time extraction encounters a record that is not present in the clinical data engine, the update handled by the real-time extraction is flagged and queued until the on-demand extraction can replicate the record to the clinical data engine.

Block 3702 includes storing the first data in a delay queue. The delay queue may be managed by the data sever or some other component of the platform 100, and may be associated with the record. In such cases, the platform will manage a distinct delay queue for each incomplete record.

Block 3703 includes after the health record is replicated in the clinical data engine, processing the delay queue to store the first data in the clinical data engine in association with the replicated health record. Note that in some cases, one or more updates in the delay queue may not need to be processed, because such updates will have already been captured during replication of the record. In such cases, only those updates in the queue that post-date the replication of the record need to be processed. The updates in need of processing can be identified in various ways, such as by examining timestamps to identify updates that occurred after a last modification date associated with the replicated health record.

Figure 3H:
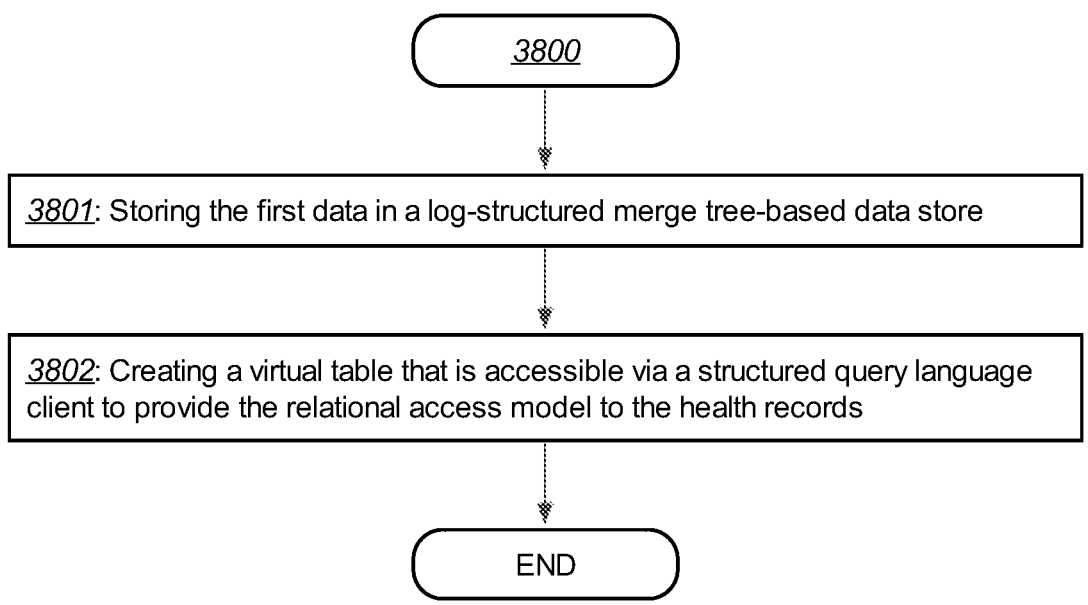

FIG. 3H is a flow diagram of example logic illustrating an extension of process 3100 of FIG. 3A. More particularly, FIG. 3H illustrates a process 3800 that includes the process 3100, wherein the storing the extracted first data includes the following block(s).

Block 3801 includes storing the first data in a log-structured merge tree-based data store. Some embodiments store the extracted data in a data store that uses a log-structured merge tree in order to provide efficient access to stored data. The use of log-structured merge trees is described further below.

Block 3802 includes creating a virtual table that is accessible via a structured query language client to provide the relational access model to the health records by converting queries received from the client into operations that traverse log-structured merge tree-based data store to retrieve data specified by constraints of the received queries. The process creates a virtual table that operates as a wrapper or interface to the underlying data in the log-structured merge tree. The virtual table automatically translates received SQL queries into operations that traverse the merge tree in order to satisfy constraints, such as those that may be specified via a SQL SELECT clause. Additional details related to the use of virtual tables is provided below.

FIG. 3I is a flow diagram of example logic for replicating electronic health records. This and the following flow diagrams illustrate extraction processes such as those described with respect to FIGS. 2A-2C, above, and as more generally described with respect to FIG. 1, above. More particularly, FIG. 3I illustrates a process 3900 that includes the following block(s).

Block 3901 includes performing extraction of first data that includes a complete health record stored by a source customer database that contains multiple electronic health records that are represented in a hierarchical data format. With reference to FIGS. 2A-2C, extraction of the first data may be extraction of one or more entire health records from the source customer database. This operation may be performed by the full extractor 102 or the on-demand extractor 103.

Block 3902 includes storing the extracted first data in a clinical data engine that represents at least some of the multiple electronic health records in a manner that logically preserves the hierarchical data format while providing a relational access model to the health records. As discussed above, the clinical data engine is hosted by the platform 100, and provides relational access to patient records obtained from the source customer database. For example, the clinical data engine may represent the hierarchical records as one or more tables, and provide a SQL or related query interface to accessing those tables.

Block 3903 includes performing real-time extraction of second data from the source customer database, wherein the first data is obtained from a journal file that includes updates to the source customer database that are based on write operations performed by a customer application to store the first data in the source customer database, and wherein the second data is obtained concurrent with the write operations performed by the customer application. With respect to FIGS. 2A-2C, extraction of the second data is typically performed by the real-time extractor 104. The real-time extractor may access the journal file by establishing a secure connection to the customer computing system that hosts the journal file, and then reading updates to the journal file via the secure connection.

Block 3904 includes storing the second data in the clinical data engine after storage of the first data. The storage of the second data is delayed until after storage of the first data. Ordering storage operations in this manner assures (1) that the relevant data record is present in the clinical data engine when the second data is stored and (2) eventual consistency between the source customer database and the clinical data engine.

Figure 3J:
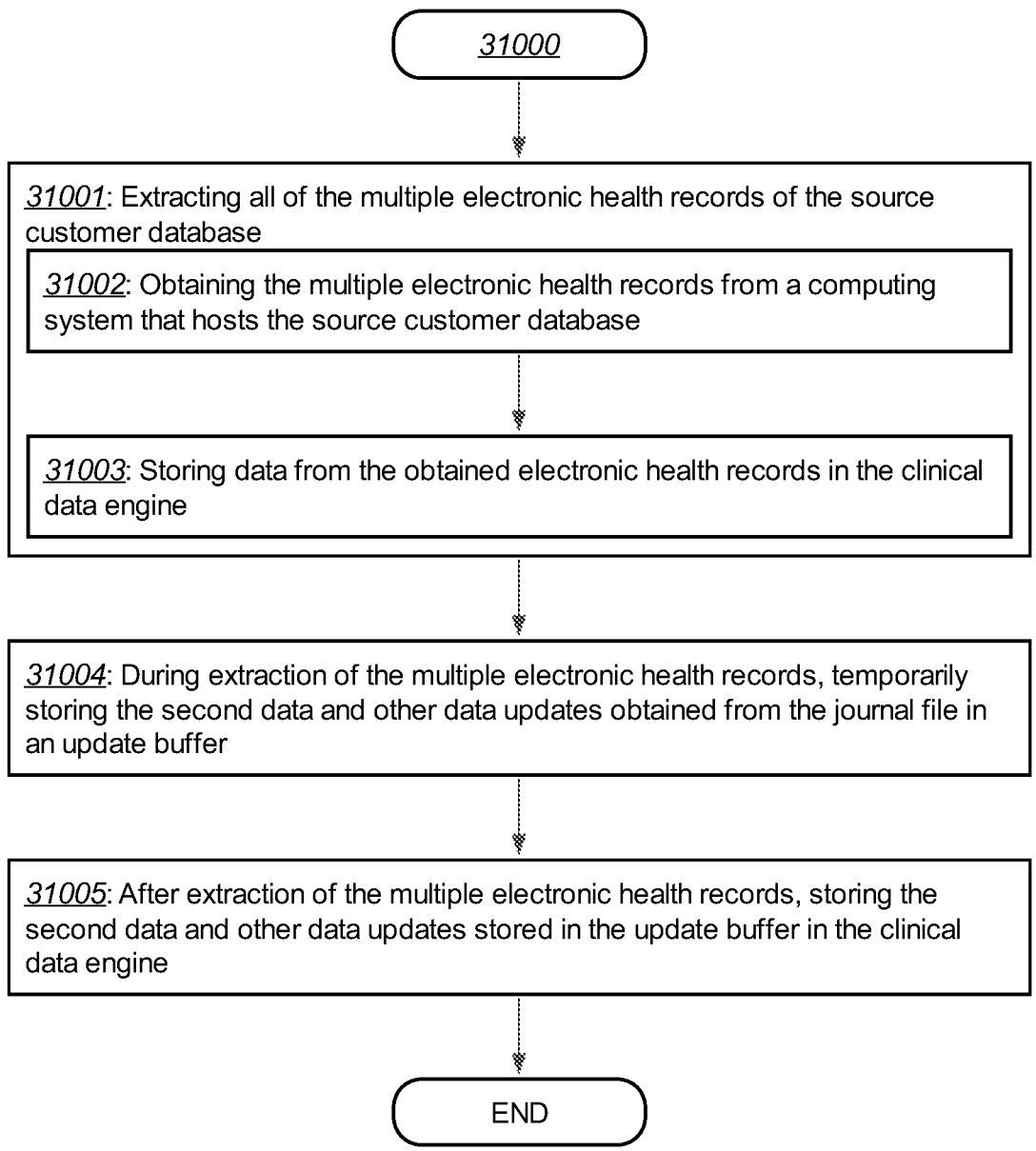

FIG. 3J is a flow diagram of example logic illustrating an extension of process 3900 of FIG. 3I. More particularly, FIG. 3J illustrates a process 31000 that includes the process 3900, and which further includes the following block(s).

Block 31001 includes extracting all of the multiple electronic health records of the source customer database by: performing block(s) 31002 and 31003, described below.

Block 31002 includes obtaining the multiple electronic health records from a computing system that hosts the source customer database. The multiple electronic health records may be obtained directly from the computing system, such as by querying the source customer database itself, by executing custom code on the source customer database that feeds records to the process, or the like. In other embodiments, the multiple electronic health records may be obtained indirectly, such as by first cloning the source customer database. The clone of the source customer database may include copies of the underlying database files used by the source customer database. Because cloning (and later extraction) of the source customer database can take some time, the real-time extraction process is initiated prior to the cloning operation in order to capture all updates to the cloned data records.

Block 31003 includes storing data from the obtained electronic health records in the clinical data engine.

Block 31004 includes during extraction of the multiple electronic health records, temporarily storing the second data and other data updates obtained from the journal file in an update buffer. The update buffer may be a log file, a database, in-memory data structure, or other storage facility that can record the second data and other updates for later replay.

Block 31005 includes after extraction of the multiple electronic health records, storing the second data and other data updates stored in the update buffer in the clinical data engine. Once the source customer database has been (directly or indirectly) extracted to the clinical data engine, the updates stored in the update buffer can be flushed or replayed in order make the clinical data engine consistent with the source customer database. Some embodiments make an optimization to minimize the size or storage of the update buffer. In this optimization, the real-time extractor may only add items to the update buffer if the corresponding record has not already been extracted (is not present in the clinical data engine). Once a record is extracted, all previously buffered updates and future updates may be written directly to the clinical data engine, bypassing the update buffer. As time passes, the clinical data engine becomes more complete, minimizing the reliance on (and storage requirements for) the update buffer. In a related technique, the update buffer may be processed prior to extraction of all records in the source customer database to identify those updates corresponding to records that have been completely extracted to the clinical data engine. The identified updates are then written to the clinical data engine. This processing may be triggered based on time (e.g., every 10 minutes), size (e.g., when the buffer reaches or exceeds a specified size), demand, or the like.

Figure 3K:
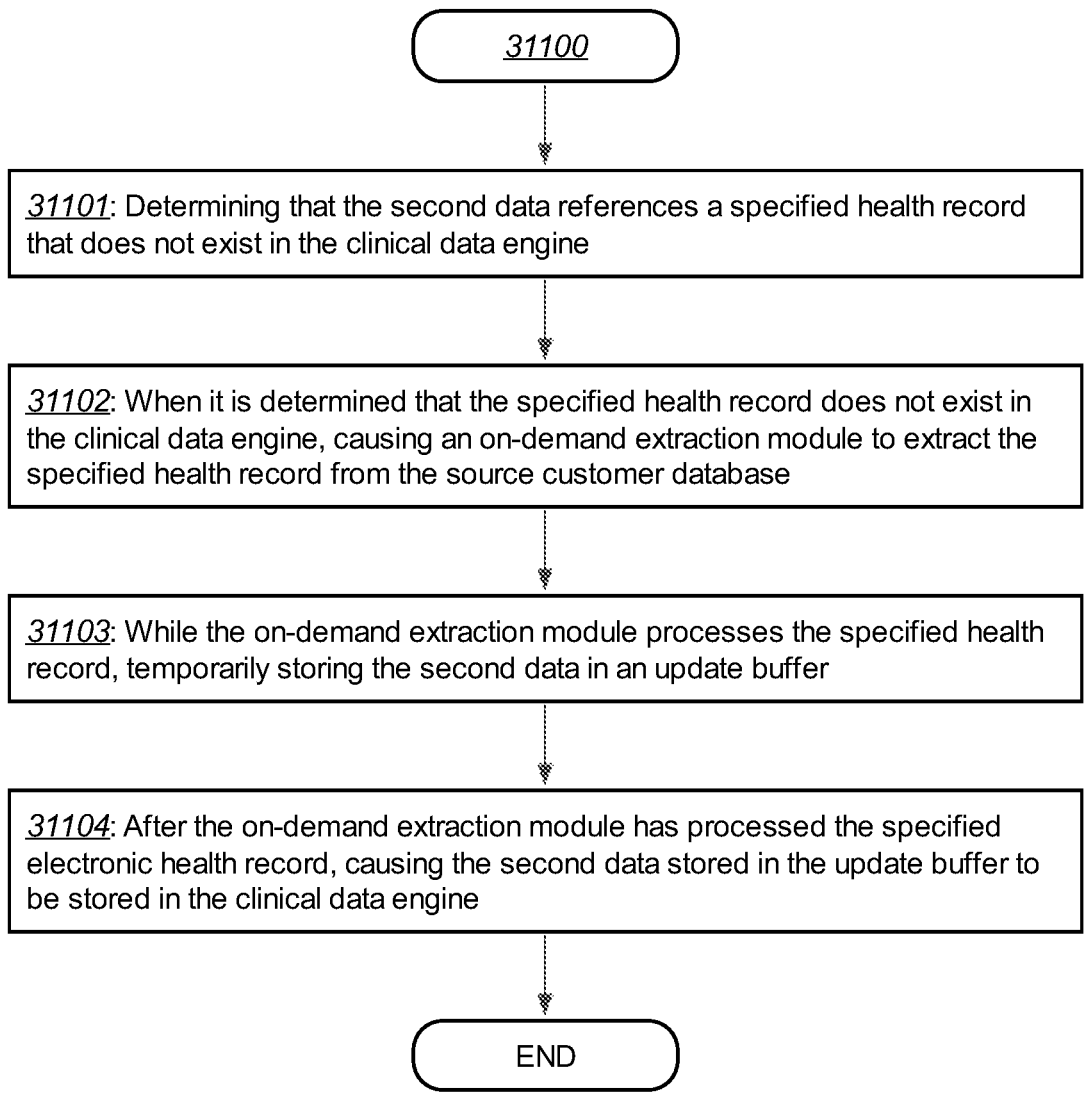

FIG. 3K is a flow diagram of example logic illustrating an extension of process 3900 of FIG. 3I. More particularly, FIG. 3K illustrates a process 31100 that includes the process 3900, and which further includes the following block(s).

Block 31101 includes determining that the second data references a specified health record that does not exist in the clinical data engine. In the context of on-demand extraction (e.g., FIG. 2C), it is possible that an update obtained from the journal file references a health record that has not yet been replicated to the clinical data engine. In this case, the update cannot be written to the clinical data engine until the corresponding record has been extracted.

Block 31102 includes when it is determined that the specified health record does not exist in the clinical data engine, causing an on-demand extraction module to extract the specified health record from the source customer database. In some embodiments, the real-time extractor notifies the on-demand extractor, such as by sending a message, making a procedure call, or the like. In response, the on-demand extractor fetches and replicates the specified health record to the clinical data engine. Upon completion of the extraction operation, the on-demand extractor notifies the real-time extractor or some other module responsible for processing the buffered updates.

Block 31103 includes while the on-demand extraction module processes the specified health record, temporarily storing the second data in an update buffer. As discussed above, any updates to the specified health record must be buffered or delayed until the underlying health record has been extracted to the clinical data engine.

Block 31104 includes after the on-demand extraction module has processed the specified electronic health record, causing the second data stored in the update buffer to be stored in the clinical data engine. As noted above, the on-demand extractor may notify the real-time extractor upon extraction of the specified heath record. In response, the real-time extractor flushes the relevant updates (e.g., those that correspond to the extracted health record) from the update buffer to the clinical data engine. In other embodiments, the on-demand extractor instead notifies the update buffer itself, which may be configured to autonomously flush the relevant updates to the clinical data engine, without intervention of the real-time extractor.

4. Access

As noted above, some embodiments provide a relational access model to the extracted data stored in the clinical data engine. In some contexts, the source customer data may be represented in a hierarchical data format. For example, the source customer data may be electronic health records that are represented in a B-tree format. The B-tree format is naturally suited to storing sparse, key-value data such as may be present in the electronic health records context. As also noted above, in at least the case of MUMPS, the source customer data may not support or provide a relational access model, such as is provided by modern SQL-based relational database systems.

Some embodiments provide relational access by initially storing the extracted data in a Log-Structured Merge ("LSM") format. The LSM format is a tree-based format that can efficiently represent sparse key-value data, such as is common in the health records context. In addition the LSM format allows for the storage of data contiguously on disk, making it ideal for recollecting data about a given data topic, such as Patient medications history. Example LSM-based storage systems include RocksDB, LevelDB, and the like. In some embodiments, such a storage system is used to implement all or part of the clinical data engine 114 of FIG. 1.

Storing the extracted data in an LSM format may include translating the extracted data from its native B-tree format into a corresponding representation for the LSM-based data store. To accomplish the translation between data stored in a B-tree format and the LSM store, the following steps are taken when a data item is copied from the source customer data to the clinical data engine. First, the incoming data item is parsed from its native (e.g., MUMPS-based) representation and divided into the items subscripts (keys) and corresponding values. The data item is typically a portion of a patient health record, such as patient contact information, patient location, a lab result, medication, a measurement (e.g., blood pressure, temperature), or the like. Second, type inference is performed for each subscript, so that an LSM-based key can be constructed for the data item. Third, the typed subscripts and corresponding values are encoded to create a respective LSM-based key and value. Finally, the key-value pair is stored in the LSM-based data store. A similar approach may be employed when reading data from the LSM-based data store given a key represented in the B-tree format. Such a read operation may be performed by the above-described extraction processes to determine whether a given item has already been extracted and is thus already present in the LSM-based data store.

Once the data is stored in the LSM-based data store, the OIP 100 can provide relational access to the stored data by performing on-the-fly translation of SQL queries/commands into corresponding access commands for the LSM-based data store. For example, a SQL query may be converted into a series of operations that traverse the LSM-based data store in order to retrieve the resulting data set specified by the SQL query. Some embodiments provide a virtual table that can be accessed by a SQL client. To a SQL client, the virtual table behaves like any other table, but internally, the virtual table invokes callbacks to perform functions against the underlying LSM-tree. Thus, a SQL query on or with respect to the virtual table results in one or more LSM-tree access operations that are performed to satisfy the constraints specified by the SQL query.

5. Example Computing System Implementation

Figure 4:
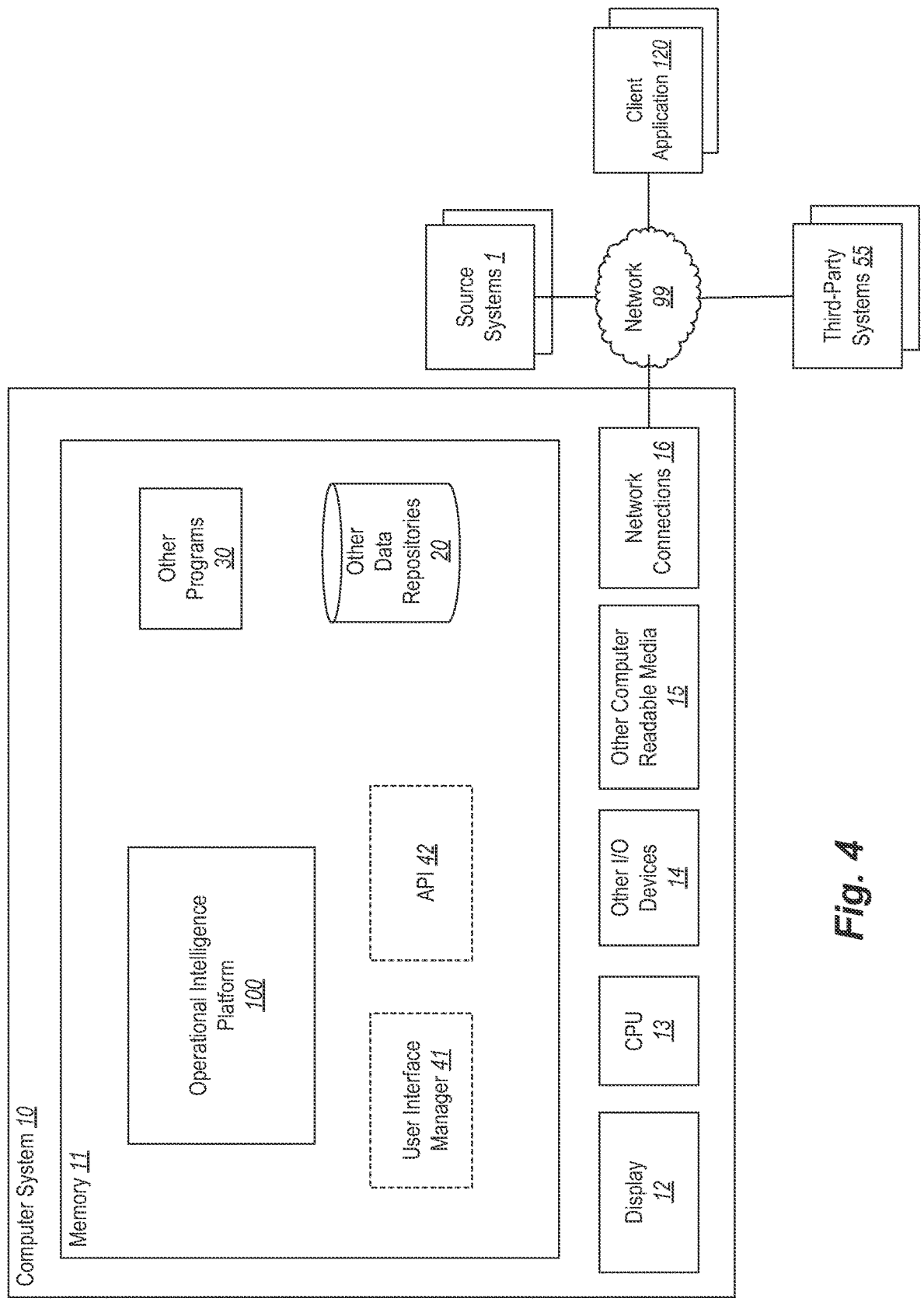
FIG. 4 is a block diagram of a computing system for implementing an operational intelligence platform according to an example embodiment.

FIG. 4 is a block diagram of a computing system for implementing an operational intelligence platform according to an example embodiment. In particular, FIG. 4 shows a computing system 10 that may be utilized to implement an OIP 100.

Note that one or more general purpose or special purpose computing systems/devices may be used to implement the OIP 100. In addition, the computing system 10 may comprise one or more distinct computing systems/devices and may span distributed locations. Furthermore, each block shown may represent one or more such blocks as appropriate to a specific embodiment or may be combined with other blocks.

Also, the OIP 100 may be implemented in software, hardware, firmware, or in some combination to achieve the capabilities described herein.

In the embodiment shown, computing system 10 comprises a computer memory ("memory") 11, a display 12, one or more Central Processing Units ("CPU") 13, Input/Output devices 14 (e.g., keyboard, mouse, CRT or LCD display, and the like), other computer-readable media 15, and network connections 16. The OIP 100 is shown residing in memory 11. In other embodiments, some portion of the contents, some or all of the components of the OIP 100 may be stored on and/or transmitted over the other computer-readable media 15. The components of the OIP 100 preferably execute on one or more CPUs 13 and perform the techniques described herein. Other code or programs 30 (e.g., an administrative interface, a Web server, and the like) and potentially other data repositories, such as data repository 20, also reside in the memory 11, and preferably execute on one or more CPUs 13. Of note, one or more of the illustrated components may not be present in any specific implementation. For example, some embodiments may not provide other computer-readable media 15 or a display 12.

The OIP 100 is shown executing in the memory 11 of the computing system 10. Also included in the memory are a user interface manager 41 and an application program interface ("API") 42. The user interface manager 41 and the API 42 are drawn in dashed lines to indicate that in other embodiments, functions performed by one or more of these components may be performed externally to the system that hosts the OIP 100.

The UI manager 41 provides a view and a controller that facilitate user interaction with the OIP 100 and its various components. For example, the UI manager 41 may provide interactive access to the OIP 100, such that users can interact with the OIP 100, such as by providing a graphical user interface that is configured to facilitate control and management of the OIP 100. In some embodiments, access to the functionality of the UI manager 41 may be provided via a Web server, possibly executing as one of the other programs 30. In such embodiments, a user operating a Web browser executing on one of the client devices 50 can interact with the OIP 100 via the UI manager 41.

The API 42 provides programmatic access to one or more functions of the OIP 100. For example, the API 42 may provide a programmatic interface to one or more functions of the OIP 100 that may be invoked by one of the other programs 30 or some other module. In this manner, the API 42 facilitates the development of third-party software, such as user interfaces, plug-ins, adapters (e.g., for integrating functions of the OIP 100 into Web applications), and the like.

In addition, the API 42 may be in at least some embodiments invoked or otherwise accessed via remote entities, such as code executing on one of the source systems 1, client applications 120, and/or third-party systems 55, to access various functions of the OIP 100. For example, the source system 1 may push records and/or data updates to the OIP 100 via the API 42. As another example, the client application 120 may query information hosted by the OIP via the API 42. The API 42 may also be configured to provide management widgets (e.g., code modules) that can be integrated into the third-party systems 55 and that are configured to interact with the OIP 100 to make at least some of the described functionality available within the context of other applications (e.g., mobile apps).

The OIP 100 interacts via the network 99 with source systems 1, client applications 120, and third-party systems/applications 55. The network 99 may be any combination of media (e.g., twisted pair, coaxial, fiber optic, radio frequency), hardware (e.g., routers, switches, repeaters, transceivers), and protocols (e.g., TCP/IP, UDP, Ethernet, Wi-Fi, WiMAX) that facilitate communication between remotely situated humans and/or devices. The third-party systems/applications 55 may include any systems that provide data to, or utilize data from, the OIP 100, including Web browsers, messaging systems, supplemental data sources, backup systems, and the like.

In an example embodiment, components/modules of the OIP 100 are implemented using standard programming techniques. For example, the OIP 100 may be implemented as a "native" executable running on the CPU 13, along with one or more static or dynamic libraries. In other embodiments, the OIP 100 may be implemented as instructions processed by a virtual machine that executes as one of the other programs 30. In general, a range of programming languages known in the art may be employed for implementing such example embodiments, including representative implementations of various programming language paradigms, including but not limited to, object-oriented (e.g., Java, C++, C#, Visual Basic.NET, Smalltalk, and the like), functional (e.g., Scala, ML, Lisp, Scheme, and the like), procedural (e.g., C, Pascal, Ada, Modula, and the like), scripting (e.g., Perl, Ruby, Python, JavaScript, VBScript, and the like), and declarative (e.g., SQL, Prolog, and the like).

The embodiments described above may also use either well-known or proprietary synchronous or asynchronous client-server computing techniques. Also, the various components may be implemented using more monolithic programming techniques, for example, as an executable running on a single CPU computer system, or alternatively decomposed using a variety of structuring techniques known in the art, including but not limited to, multiprogramming, multithreading, client-server, or peer-to-peer, running on one or more computer systems each having one or more CPUs. Some embodiments may execute concurrently and asynchronously, and communicate using message passing techniques. Equivalent synchronous embodiments are also supported. Also, other functions could be implemented and/or performed by each component/module, and in different orders, and by different components/modules, yet still achieve the described functions.

In addition, programming interfaces to the data stored as part of the OIP 100, such as in the configuration data 112, clinical data engine 114, and/or the other data repositories 20, can be available by standard mechanisms such as through C, C++, C#, and Java APIs; libraries for accessing files, databases, or other data repositories; through scripting languages such as XML; or through Web servers, FTP servers, or other types of servers providing access to stored data. The configuration data 112, clinical data engine 114, and the other data repositories 20 may be implemented as one or more database systems, file systems, or any other technique for storing such information, or any combination of the above, including implementations using distributed computing techniques.

Different configurations and locations of programs and data are contemplated for use with techniques of described herein. A variety of distributed computing techniques are appropriate for implementing the components of the illustrated embodiments in a distributed manner including but not limited to TCP/IP sockets, RPC, RMI, HTTP, Web Services (XML-RPC, JAX-RPC, SOAP, and the like). Other variations are possible. Also, other functionality could be provided by each component/module, or existing functionality could be distributed amongst the components/modules in different ways, yet still achieve the functions described herein.

Furthermore, in some embodiments, some or all of the components of the OIP 100 may be implemented or provided in other manners, such as at least partially in firmware and/or hardware, including, but not limited to one or more application-specific integrated circuits ("ASICs"), standard integrated circuits, controllers executing appropriate instructions, and including microcontrollers and/or embedded controllers, field-programmable gate arrays ("FPGAs"), complex programmable logic devices ("CPLDs"), and the like. Some or all of the system components and/or data structures may also be stored as contents (e.g., as executable or other machine-readable software instructions or structured data) on a computer-readable medium (e.g., as a hard disk; a memory; a computer network or cellular wireless network or other data transmission medium; or a portable media article to be read by an appropriate drive or via an appropriate connection, such as a DVD or flash memory device) so as to enable or configure the computer-readable medium and/or one or more associated computing systems or devices to execute or otherwise use or provide the contents to perform at least some of the described techniques. Some or all of the components and/or data structures may be stored on tangible, non-transitory storage mediums. Some or all of the system components and data structures may also be stored as data signals (e.g., by being encoded as part of a carrier wave or included as part of an analog or digital propagated signal) on a variety of computer-readable transmission mediums, which are then transmitted, including across wireless-based and wired/cable-based mediums, and may take a variety of forms (e.g., as part of a single or multiplexed analog signal, or as multiple discrete digital packets or frames). Such computer program products may also take other forms in other embodiments. Accordingly, embodiments of this disclosure may be practiced with other computer system configurations.

All of the above U.S. patents, U.S. patent application publications, U.S. patent applications, foreign patents, foreign patent applications, non-patent publications, and appendixes referred to in this specification and/or listed in the Application Data Sheet are incorporated herein by reference, in their entireties.

From the foregoing it will be appreciated that, although specific embodiments have been described herein for purposes of illustration, various modifications may be made without deviating from the spirit and scope of this disclosure. Also, the methods, techniques, and systems discussed herein are applicable to differing protocols, communication media (optical, wireless, cable, etc.) and devices (e.g., desktop computers, wireless handsets, electronic organizers, personal digital assistants, tablet computers, etc.).

The invention claimed is:

1. A system for replicating electronic health records from a source customer database that contains multiple electronic health records that are represented in a hierarchical data format, the system comprising:

a processor;
a memory;
a first extraction module comprising instructions that are stored in the memory and that are configured, when executed by the processor, to:
   perform extraction of first data from the source customer database, wherein the first data includes a complete data record stored by the source customer database; and
   cause the extracted first data to be stored in a clinical data engine that represents at least some of the multiple electronic health records in a manner that logically preserves the hierarchical data format while providing a relational access model to the health records; and
a second extraction module comprising instructions that are stored in the memory and that are configured, when executed by the processor, to:
   perform real-time extraction of second data from the source customer database, wherein the second data is obtained from a journal file of the source customer database, wherein the source customer database stores the second data in the journal file in response to write operations performed by a customer application to store the second data in the source customer database, and wherein the second data is obtained by the second extraction module concurrent with the write operations performed by the customer application;
   determine that the second data is an update that references the complete data record stored by the source customer database;
   determine, by querying the clinical data engine, that the complete data record referenced by the update does not exist in the clinical data engine;
   in response to the determination that the complete data record does not exist in the clinical data engine:
      flag and place the update that references the complete data record in a delay queue associated with the complete data record;
      transmit to the first extraction module an instruction to extract the complete data record stored by the source customer database, wherein the first extraction module stores the complete data record in the clinical data engine; and
      while the first extraction module extracts the complete data record, temporarily store the second data in the delay queue;
   after the first extraction module has extracted the complete data record, cause the second data stored in the delay queue to be stored in the clinical data engine; and
   cause the extracted second data to be stored in the clinical data engine after storage of the complete data record in the first data.

2. The system of claim 1, wherein the first extraction module is a full extraction module that is configured to:
   obtain the multiple electronic health records from a customer computing system that hosts the source customer database; and
   store data from the obtained electronic health records in the clinical data engine.

3. The system of claim 2, wherein the second extraction module is a real-time extraction module that is configured to:
   while the full extraction module processes the electronic health records of the source customer database, temporarily store the second data and other data updates obtained from the journal file in the delay queue; and after the full extraction module has processed all of the electronic health records of the source customer database, cause the second data and other data updates stored in the delay queue to be stored in the clinical data engine.

4. The system of claim 1, wherein the first extraction module is a full extraction module that is configured to:
obtain the electronic health records from a clone of the source customer database, wherein the clone is hosted by the system for replicating electronic health records; and
wherein the second extraction module is executed prior to the first extraction module in order to capture data updates made to the source customer database during construction of the clone and during extraction of the health records from the clone to the clinical data engine by the first extraction module.

5. The system of claim 1, wherein the first extraction module is an on-demand extraction module that is configured to:
receive the instruction to extract the complete data record from the source customer database;
in response to the received instruction, obtain the complete data record from the source customer database; and
store data from the complete data record in the clinical data engine.

6. The system of claim 1, wherein the second extraction module is initiated prior to initiation of the first extraction module, such that the second extraction module captures updates to the source customer database that occur during the extraction performed by the first extraction module.

7. A method for replicating electronic health records, the method comprising:
performing extraction of first data that includes a complete health record stored by a source customer database that contains multiple electronic health records that are represented in a hierarchical data format;
storing the extracted first data in a clinical data engine that represents at least some of the multiple electronic health records in a manner that logically preserves the hierarchical data format while providing a relational access model to the health records;
performing real-time extraction of second data from the source customer database, wherein the first data is obtained from a journal file of the source customer database, wherein the source customer database stores the second data in the journal file in response to write operations performed by a customer application to store the first data in the source customer database, and wherein the second data is obtained concurrent with the write operations performed by the customer application;
determining that the second data is an update that references a specified health record that is stored by the source customer database;
determining, by querying the clinical data engine, that the specified health record referenced by the update does not exist in the clinical data engine;
in response to the determining that the specified health record does not exist in the clinical data engine:
flag and place the update that references the specified health record in a delay queue associated with the specified data record;
causing an on-demand extraction module to extract the specified health record from the source customer database, wherein the on-demand extraction module stores the specified health record in the clinical data engine; and
while the on-demand extraction module extracts the specified health record, temporarily storing the second data in the delay queue;
after the on-demand extraction module has extracted the specified electronic health record, causing the second data stored in the delay queue to be stored in the clinical data engine; and
storing the second data in the clinical data engine after storage of the first data.

8. The method of claim 7, further comprising:
extracting all of the multiple electronic health records of the source customer database by:
obtaining the multiple electronic health records from a computing system that hosts the source customer database; and
storing data from the obtained electronic health records in the clinical data engine;
during extraction of the multiple electronic health records, temporarily storing the second data and other data updates obtained from the journal file in the delay queue; and
after extraction of the multiple electronic health records, storing in the clinical data engine the second data and other data updates stored in the delay queue.

9. The method of claim 8, wherein the extracting all of the multiple electronic health records of the source customer database includes:
creating a clone of the source customer database by obtaining a copy of the multiple electronic health records of the source customer database; and
obtaining the multiple electronic health records from the clone of the source customer database, wherein the clone is hosted by a computing system that performs the method.

10. The method of claim 7, wherein the first data includes the specified health record.

11. The method of claim 7, further comprising:
storing multiple updates to the specified health record in the delay queue; and
after storage of the first data in the clinical data engine, flushing the delay queue to the clinical data engine, wherein flushing the delay queue includes storing in the clinical data engine only those updates that have occurred after storage of the first data.

12. The method of claim 7, wherein the performing real-time extraction of second data from the source customer database is initiated prior to initiation of the performing extraction of first data that includes a complete health record.

13. The method of claim 7, further comprising:
initiating execution of a real-time extraction module that is responsible for performing real-time extraction of second data from the source customer database; and
after initiation of the real-time extraction module, initiating execution of a full extraction module that is responsible for performing extraction of first data that includes a complete health record.

14. The method of claim 13, further comprising: after the full extraction module has processed all of the health records from the source customer database, terminating the full extraction module and continuing to process updates obtained from the journal file.

15. The method of claim 7, further comprising:
initiating execution of a real-time extraction module that is responsible for performing real-time extraction of second data from the source customer database;
after initiation of the real-time extraction module, initiating execution of an on-demand extraction module that is responsible for performing extraction of first data that includes a complete health record; and
wherein the real-time extraction module is configured to cause the on-demand extraction module to extract an electronic health record referenced by the second data when the electronic health record does not exist in the clinical data engine.

16. The method of claim 7, further comprising:
initiating execution of a real-time extraction module that is responsible for performing real-time extraction of second data from the source customer database;
in response to termination of the real-time extraction module,
determining a last time at which an update was successfully made to the clinical data engine;
processing historical journal file data created after the determined time; and
after processing the historical journal file data, continuing real-time extraction of second data from the source customer database.

17. The method of claim 16, wherein continuing real-time extraction of second data from the source customer database includes:
restarting the real-time extraction module;
noting a timestamp or identifier of a first update processed by the restarted real-time extraction module; and
processing historical journal file data until the noted timestamp or identifier is encountered.

18. The method of claim 7, further comprising:
during extraction of a complete data record,
storing in a delay queue multiple updates to the complete data record, wherein the delay queue is associated with the complete data record; and
associating a timestamp with each of the multiple updates stored in the delay queue; and
after extraction of the complete data record, storing in the clinical data engine only those updates that have timestamps that are later than a last modification time of the complete data record.

19. A non-transitory computer-readable medium including contents that are configured, when executed, to cause a computing system to perform a method for replicating electronic health records, the method comprising:
performing extraction of first data that includes a complete health record stored by a source customer database that contains multiple electronic health records that are represented in a hierarchical data format;
storing the extracted first data in a clinical data engine that represents at least some of the multiple electronic health records in a manner that logically preserves the hierarchical data format while providing a relational access model to the health records;
performing real-time extraction of second data from the source customer database, wherein the first data is obtained from a journal file of the source customer database, wherein the source customer database stores the second data in the journal file in response to write operations performed by a customer application to store the first data in the source customer database, and wherein the second data is obtained concurrent with the write operations performed by the customer application;
determining that the second data is an update that references a specified health record that is stored by the source customer database;
determining, by querying the clinical data engine, that the specified health record referenced by the update does not exist in the clinical data engine;
in response to the determining that the specified health record does not exist in the clinical data engine;
flag and place the update that references the specified health record in a delay queue associated with the specified data record;
causing an on-demand extraction module to extract the specified health record from the source customer database, wherein the on-demand extraction module stores the specified health record in the clinical data engine; and
while the on-demand extraction module extracts the specified health record, temporarily storing the second data the delay queue;
after the on-demand extraction module has extracted the specified electronic health record, causing the second data stored in the delay queue to be stored in the clinical data engine; and
storing the second data in the clinical data engine after storage of the first data.

* * * * *